US006490474B1

(12) United States Patent
Willis et al.

(10) Patent No.: US 6,490,474 B1
(45) Date of Patent: *Dec. 3, 2002

(54) SYSTEM AND METHOD FOR ELECTRODE LOCALIZATION USING ULTRASOUND

(75) Inventors: N. Parker Willis, Atherton, CA (US); Axel Brisken, Fremont, CA (US); Jinglin Zeng, San Jose, CA (US); Marsha Hurd, Clayton, CA (US)

(73) Assignee: Cardiac Pathways Corporation, Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/905,090

(22) Filed: Aug. 1, 1997

(51) Int. Cl.$^7$ .................................................. A61B 5/04
(52) U.S. Cl. ....................... 600/424; 600/374; 607/122; 606/41
(58) Field of Search ................................ 600/424, 374, 600/373, 509; 607/122, 126; 606/41, 45, 49, 32, 34

(56) References Cited

U.S. PATENT DOCUMENTS

| 4,100,916 A | 7/1978 | King | 128/2 V |
|---|---|---|---|
| 4,173,228 A | 11/1979 | Van Steenwyk et al. | 128/653 |
| 4,304,239 A | 12/1981 | Perlin | 128/642 |
| 4,431,005 A | 2/1984 | McCormick | 128/656 |
| 4,444,195 A | 4/1984 | Gold | 128/642 |
| 4,499,493 A | 2/1985 | Nishimura | 358/111 |
| 4,522,212 A | 6/1985 | Gelinas et al. | 128/642 |
| 4,573,473 A | 3/1986 | Hess | 128/642 |
| 4,613,866 A | 9/1986 | Blood | 343/448 |
| 4,628,937 A | 12/1986 | Hess et al. | 128/642 |
| 4,649,924 A | 3/1987 | Taccardi | 128/642 |

(List continued on next page.)

FOREIGN PATENT DOCUMENTS

| EP | 0 499 491 A2 | 8/1992 | A61N/1/05 |
|---|---|---|---|
| EP | 775 466 A2 | 5/1997 | A61B/5/04 |

OTHER PUBLICATIONS

Borg, I. et al., *Multidimensional Similarity Structure Analysis*, New York; Springer Verlay, 1987, pp. 309–329.

Klein, R. et al., "A System for 3D Tracking of Limb Movement," Proceedings of the Ninth Annual Conference of the IEEE Engineering in Medicine and Biology Society, Nov. 13–16, 1987, vol 4.

(List continued on next page.)

*Primary Examiner*—Ruth S. Smith
(74) *Attorney, Agent, or Firm*—Bingham McCutchen LLP

(57) ABSTRACT

The present invention is a device localization system that uses one or more ultrasound reference catheters to establish a fixed three-dimensional coordinate system within a patient's heart using principles of triangulation. The coordinate system is represented graphically in three-dimensions on a video monitor and aids the clinician in guiding other medical devices, which are provided with ultrasound transducers, through the body to locations at which they are needed to perform clinical procedures. In one embodiment of a system according to the present invention, the system is used in the heart to help the physician guide mapping catheters for measuring electrical activity, and ablation catheters for ablating selected regions of cardiac tissue, to desired locations within the heart.

83 Claims, 26 Drawing Sheets

U.S. PATENT DOCUMENTS

| 4,697,595 A | 10/1987 | Breyer et al. | 128/660 |
|---|---|---|---|
| 4,699,147 A | 10/1987 | Chilson et al. | 128/642 |
| 4,777,955 A | 10/1988 | Brayton et al. | 128/642 |
| 4,785,817 A | 11/1988 | Stouffer | 128/660.07 |
| 4,812,976 A | 3/1989 | Lundy | 354/413.06 |
| 4,821,206 A | 4/1989 | Arora | 364/513 |
| 4,821,731 A | 4/1989 | Martinelli et al. | 128/662.06 |

| | | | |
|---|---|---|---|
| 4,899,750 A | 2/1990 | Ekwall | 128/419 PG |
| 4,922,912 A | 5/1990 | Watanabe | 128/642 |
| 4,940,064 A | 7/1990 | Desai | 128/784 |
| 4,945,305 A | 7/1990 | Blood | 324/207.17 |
| 5,000,190 A | 3/1991 | Petre | 128/713 |
| 5,012,814 A | 5/1991 | Mills et al. | 128/691 |
| 5,025,786 A | 6/1991 | Siegel | 128/642 |
| 5,041,973 A | 8/1991 | Lebron et al. | 364/413.05 |
| 5,042,486 A | 8/1991 | Pfeiler et al. | 128/653 R |
| 5,054,492 A | 10/1991 | Scribner et al. | 128/662.06 |
| 5,054,496 A | 10/1991 | Wen et al. | 128/696 |
| 5,056,517 A | 10/1991 | Fenici | 128/419 P |
| 5,081,993 A | 1/1992 | Kitney et al. | 128/661.08 |
| 5,104,393 A | 4/1992 | Isner et al. | 606/15 |
| 5,107,746 A | 4/1992 | Bauer | 84/626 |
| 5,154,501 A | 10/1992 | Svenson et al. | 128/419 D |
| 5,156,151 A | 10/1992 | Imran | 128/642 |
| 5,158,092 A | 10/1992 | Glace | 128/705 |
| 5,161,536 A | 11/1992 | Vilkomerson et al. | 128/660.07 |
| 5,172,699 A | 12/1992 | Svenson et al. | 128/705 |
| 5,214,615 A | 5/1993 | Bauer | 367/128 |
| 5,220,924 A | 6/1993 | Frazin | 128/662.06 |
| 5,222,501 A | 6/1993 | Ideker et al. | 128/660.03 |
| 5,246,016 A | 9/1993 | Lieber et al. | 128/898 |
| 5,295,484 A | 3/1994 | Marcus et al. | 128/660.03 |
| 5,297,549 A | 3/1994 | Beatty et al. | 128/642 |
| 5,311,873 A | 5/1994 | Savard et al. | 128/696 |
| 5,335,663 A | 8/1994 | Oakley et al. | 128/662 |
| 5,341,807 A | 8/1994 | Nardella | 128/642 |
| 5,357,956 A | 10/1994 | Nardella | 128/642 |
| 5,367,614 A | 11/1994 | Bisey | 395/119 |
| 5,385,148 A | 1/1995 | Lesh et al. | 128/662.06 |
| 5,391,199 A | 2/1995 | Ben-Haim | 607/122 |
| 5,412,619 A | 5/1995 | Bauer | 367/128 |
| 5,443,489 A | 8/1995 | Ben-Haim | 607/115 |
| 5,480,422 A | 1/1996 | Ben-Haim | 607/122 |
| 5,515,853 A | 5/1996 | Smith et al. | 128/661.01 |
| 5,546,951 A | 8/1996 | Ben-Haim | 128/702 |
| 5,553,611 A | 9/1996 | Budd et al. | 128/642 |
| 5,588,432 A | 12/1996 | Crowley | 128/660.03 |
| 5,590,657 A | 1/1997 | Cain et al. | 128/660.03 |
| 5,669,878 A | 9/1997 | Dickinson et al. | 604/95 |
| 5,722,402 A * | 3/1998 | Swanson et al. | 607/122 |
| 5,779,638 A | 7/1998 | Vesely et al. | |
| 5,782,899 A * | 7/1998 | Imran | 607/122 |
| 5,797,849 A | 8/1998 | Vesely et al. | |
| 5,868,673 A * | 2/1999 | Vesely | 600/407 |
| 5,938,602 A | 8/1999 | Lloyd | 600/424 |
| 5,954,649 A * | 9/1999 | Chia et al. | 600/424 |

OTHER PUBLICATIONS

Young, A.A. et al., "Epicardial Surface Estimation from Coronary Angiograms," *Computer Vision, Graphics, and Image Processing,* vol. 47, 1989, pp. 111–127.

Moshage, W. et al., "Biomagnetic Localization of Ventricular Arrhythmias," *Radiology,* Sep. 1991, pp. 685–692.

Fenici, R., et al., "Biomagnetically localizable multipurpose catheter and method for MCG guided intracardiac electrophysiology, biopsy and ablation of cardiac arrhythmias," *International J ournal of Cardiac Imaging,* 1991, vol. 7, pp. 207–215.

Ruprecht, Detlef et al., "Spatial Free–Form Deformation with Scattered Data Interpolation Methods," Computer & Graphics, vol. 19, No. 1, 1995, pp. 63–71.

Denney Jr., Thomas S. et al., "Reconstruction of 3–D Left Ventricular Motion from Planar Tagged Cardiac MR Images: An Estimation Theoretic Approach," *IEEE Transactions on Medical Imaging,* vol. 14, No. 4, 1995, pp. 625–635.

Clarysse, P. et al., "3D Boundary Extraction of the Left Ventricle by a Deformable Model with A Priori Information," IEEE, 1995, pp. 492–495.

de Zwart, M. et al., "Endocardial Catheter Mapping–Development of An Interactive Expert System for the Measurement of Local Activation and 3–Dimensional Electrode Position," *IEEE*, 1988, pp. 105–108.

Smith, W. et al., "Three Dimensional Ultrasonic Micrometer for Use in Cardiovascular Research," Annual International Conference of the IEEE Engineering in Medicine and and Biology Society, vol. 13, No. 4, 1991, pp. 1520–1521.

Gubbels, Andrew, "Sonomicrometer Enhancement Implementing 16–Bit Counters into EPLDs," E.S. 400—Project Report, Mar. 25, 1993, pp. 1–72.

Klein, R., et al., "A System For 3D Tracking of Limb Movement," (1990)*IEEE*, Ninth Ann. Conf. of Eng. in Med. & Biol. Sci. (2 pages).

Langberg, J. et al., "The Echo–Transponder Electrode Catheter: A New Method for Mapping the Left Ventricle," *JACC,* vol. 12, No. 1, Jul. 1988, pp. 218–223.

Fenici, R., et al., "Catheter Ablation of Cardiac Arrhythmias: Magnetocardiographic Localization of Electrocatheters and Arrhythmogenic Foci," 8th Internatioanl Congress "The New Frontiers of Arrhythmias," Marilleva, Italy, Jan. 31–Feb. 6, 1988, pp. 723–731.

Fenici, R., et al. "Magnetocardiographic Localization of a Pacing Catheter," *Advances in Biomagnetism,* 1989, pp. 361–364.

Moshage, W. et al., "Biomagnetic Localization of Ventricular Arrhythmias[1]," *Radiology,* Sep. 1991, pp. 685–692.

Potratz, J. et al., "Echocardiographic Guiding of Catheter–Electrode During Endocardial Mapping to Determine Location of Late Fractionated Potentials in Patients with Acute Myocardial Infarction," *European Heart Journal,* vol. 12, Abstract Supplement p. 235, abstract 1242 (Aug. 1991).

Fenici, R., et al., "Biomagnetically localizable multipurpose catheter and method for MCG guided intracardiac electrophysiology, biopsy and ablation of cardiac arrhythmias," *International Journal of Cardiac Imaging,* 1991, vol. 7, pp. 207–215.

Saumarez, R. et al., "Geometrically Accurate Transaortic Mapping of Left Ventricular Endocardial Activation During Surgery," *JACC,* vol. 19, No. 1, Jan. 1992, pp. 125–129.

Aoyagi, S. et al., "Using Ultrasonic Waves," *IEEE,* (1991) pp. 2466–2471.

Cikes, I., et al., "Cardiac Catheterization Guided By Ultrasound," *Echocardiography in Cardiac Interventions,* 1989., pp. 77–88.

Ferek–Petric, B., et al. "Ultrasonically Marked Pacing System," *Echocardiography in Cardiac Interventions,* 1989, pp. 89–97.

Sonomicrometer Module—Model 201, Product Information Sheets (6 pages) Triton Technology, Inc., 1995.

Fenici, R, et al., "Clinical Magnetocardiography Localization of Arrhytmogenic Structure," Clinical Physiology—Cardiovascular Biomagnetism Unit C.N.R. Catholic University of S. Heart, L. go A. Gemelli, Rome, Itally, pp. 102–118.

Josephson, M. et al., "Role of Catheter Mapping in the Preoperative Evaluation of Ventricular Tachycardia," *The American Journal of Cardiology,* Jan. 1982, vol. 49, pp. 207–220.

Josephson, M. et al., "Comparison of Endocardial Catheter Mapping with Intraoperative Mapping of Ventricular Tachycardia," *Circulation,* vol. 61, No. 2, Feb. 1980, pp. 396–404.

Josephson, M. et al., "Ventricular Activation During Ventricular Endocardial Pacing. II. Role of Pace–Mapping to Localize Origin of Ventricular Tachycardia," *The American Journal of Cardiology*, Jul. 1982, vol. 50, pp. 11–22.

Witkowski, F., et al., "An Automated Simultaneous Transmural Cardiac Mapping System," *The American Physiological Society*, 1984, pp. H661–H668.

Fann, J. et al., "Endocardial Activation Mapping and Endocardial Pace–Mapping Using a Balloon Apparatus," *Amer. J. Cardiol.*, vol. 55, Apr. 1, 1985, pp. 1076–1083.

Hauer, R. et al., "Endocardial Catheter Mapping: Wire Skeleton technique for Representation of Computed Arrhythmogenic Sites Compared With Intraoperative Mapping," *Circulation*, vol. 74, No. 6, Dec. 1986, pp. 1346–1354.

Pogwizd, S. et al., "Reentrant and Nonreentrant Mechanisms Contribute to Arrhythmogenesis During Early Myocardial Ischemia: Results Using Three–Dimensional Mapping," *Circulation Research*, vol. 61, No. 3, pp. 352–371.

Huang, S. et al., "Radiofrequency Catheter Ablation of the Left and Right Ventricles: Anatomic and Electrophysiologic Observations," *Pace*, vol. 11, Apr. 1988, pp. 449–459.

Jackman, W. et al., "New Catheter Technique for Recording Left Free–Wall Accessory Atrioventricular Pathway Activation," *Circulation*, Sep. 1988, vol. 78, No. 3, pp. 598–611.

Pagé, P. et al., "Surgical Treatment of Ventricular Tachycardia," *Circulation*, Sep. 1989, vol. 80 (suppl I) pp. I–124–I–134.

Tweddell, J. et al., "Potential Mapping in Septal Tachycardia," *Circulation*, Sep. 1989, vol. 80 (suppl I) pp. I–97–I–108.

Shenasa, M. et al., "Cardiac Mapping. Part I: Wolff–Parkinson–White Syndrome," *Pace*, vol. 13 Feb. 1990, pp. 223–230.

Scheinman, M. "Current Role of Catheter Ablative Procedures in Patients With Cardiac Arrhythmias," *Circulation*, vol. 83, No. 6, Jun. 1991, pp. 2146–2153.

Buckles, D. et al., "Computer–Enhanced Mapping of Activation Sequences in the Surgical Treatment of Supraventricular Arrhythmias," *Pace*, vol. 13, Nov. 1990, pp. 1401–1407.

Tanigawa, M. et al., "Prolonged and Fractionated Right Atrial Electrograms During Sinus Rhythm in Patients With Paroxysmal Atrial Fibrillation and Sick Sinus Node Syndrome," *The American College of Cardiology*, Feb. 1991, vol. 17, No. 2, pp. 403–408.

Kaltenbrunner, W. et al., "Epicardial and Endocardial Mapping of Ventricular Tachycardia in Patient With Myocardial Infarction," *Circulation*, Sep. 1991, vol. 84, No. 3, pp. 1058–1071.

Massé, S. et al., "A Three–Dimensional Display for Cardiac Activation Mapping," *Pace*, vol. 14, Apr. 1991, Part I, pp. 538–545.

Desai, J. et al., "Orthogonal Electrode Catheter Array for Mapping of Endocardial Focal Site of Ventricular Activation," *Pace*, vol. 14, Apr. 1991, Part I, pp. 557–574.

Pollak, S. et al., "Intraoperative Identification of a Radiofrequency Lesion Allowing Validation of Catheter Mapping of Ventricular Tachycardia with a Computerized Balloon Mapping System," *Pace*, vol. 15, Jun. 1992, pp. 854–858.

Chen, S. et al., "Reaapraisal of Electrical Cure of Atrioventricular Nodal Reentrant Tachycardia—Lessons From a Modified Catheter Ablation Technique," *International Journal of Cardiology*, (1992) vol. 37, pp. 51–60.

Chen, S. et al., "Radiofrequency Catheter Ablation For Treatment of Wolff–Parkinson–White Syndrome—Short– and Long–term Follow–up," *International Journal of Cardiology*, vol. 37 (1992) pp. 199–207.

Scheinman, M. "North American Society of Pacing and Electrophysiology (NASPE) Survey on Radiofrequency Catheter Ablation: Implications for Clinicians, Third Party Insurers, and Government Regulatory Agencies," *Pace*, vol. 15, Dec. 1992, pp. 2228–2231.

Silka, M. et al., "Phase Image Analysis of Anomalous Ventricular Activation in Pediatric Patients With Preexcitation Syndromes or Ventricular Tachycardia," *American Heart Journal*, Feb. 1993, vol. 125, pp. 372–380.

Josephson, M., "Recurrent Ventricular Tachycardia," pp. 566–580; 608–615; and "Surgical and Nonsurgical Ablation in the Therapy of Arrhythmias," pp. 770–783, *Clinical Cardiac Electrophysiology: Techniques and Interpretations*, Sec. Ed., Lea & Febiger, 1993.

Kuchar, D. et al., "Electrocardiographic Localization of the Site of Origin of Ventricular Tachycardia in Patients With Prior Myocardial Infarction," *JACC*, Mar. 15, 1989, vol. 13, No. 4, pp. 893–900.

Holt, P. et al., "Ventricular Arrhytmias," *British Heart Journal*, 1985, vol. 53, pp. 417–430.

Ratcliffe, M. et al., "Use of Sonomicrometry and Multidimensional Scaling to Determine the Three–Dimensional Coordinates of Multiple Cardiac Locations: Feasibility and Initial Implementation," *IEEE Transactions on Biomedical Engineering*, vol. 42, No. 6, Jun. 1995, pp. 587–598.

Meyer, S. et al., "Application of Sonomicrometry and Multidimensional Scaling to Cardiac Catheter Tracking," *IEEE Transactions on Biomedical Engineering*, vol. 44, No. 11, Nov. 1997, pp. 1061–1067.

\* cited by examiner

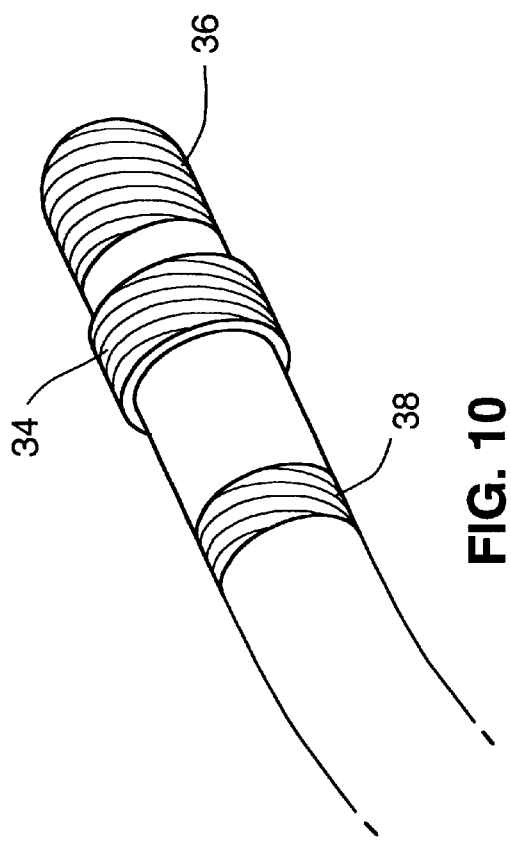
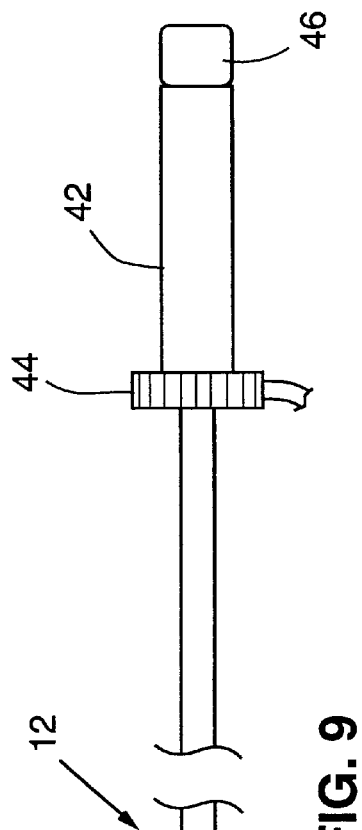
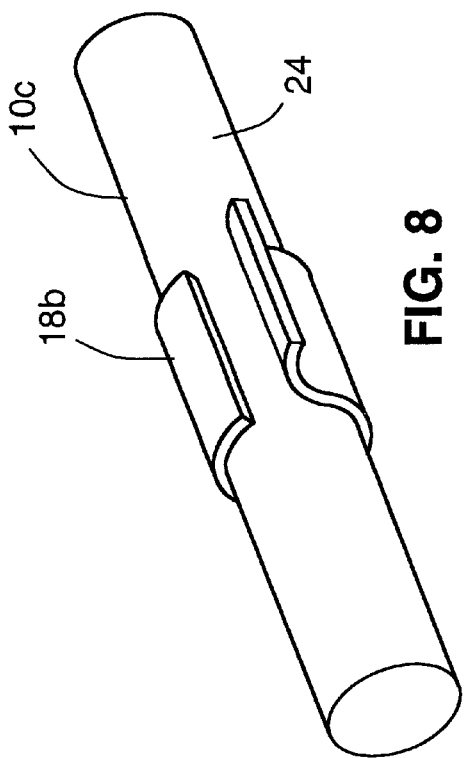
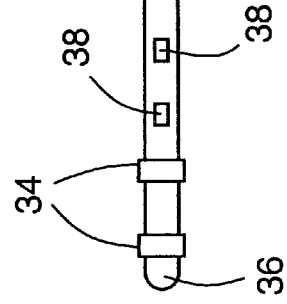
FIG. 8
FIG. 10
FIG. 9

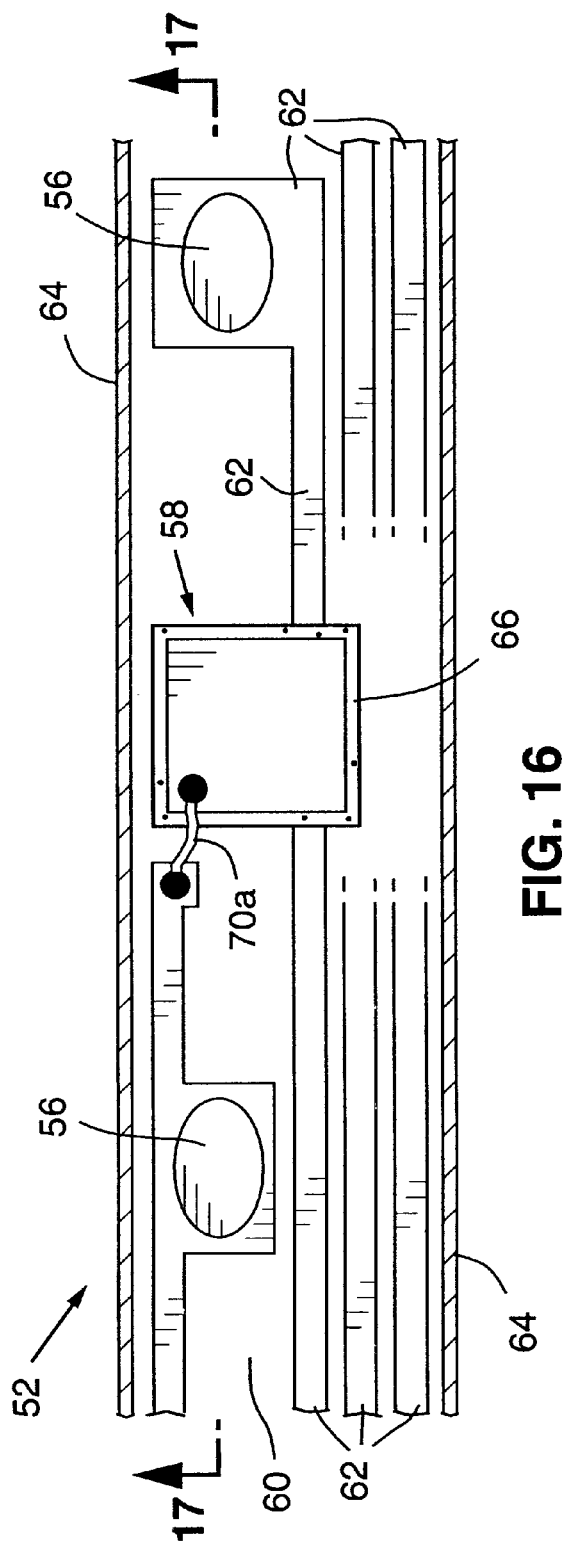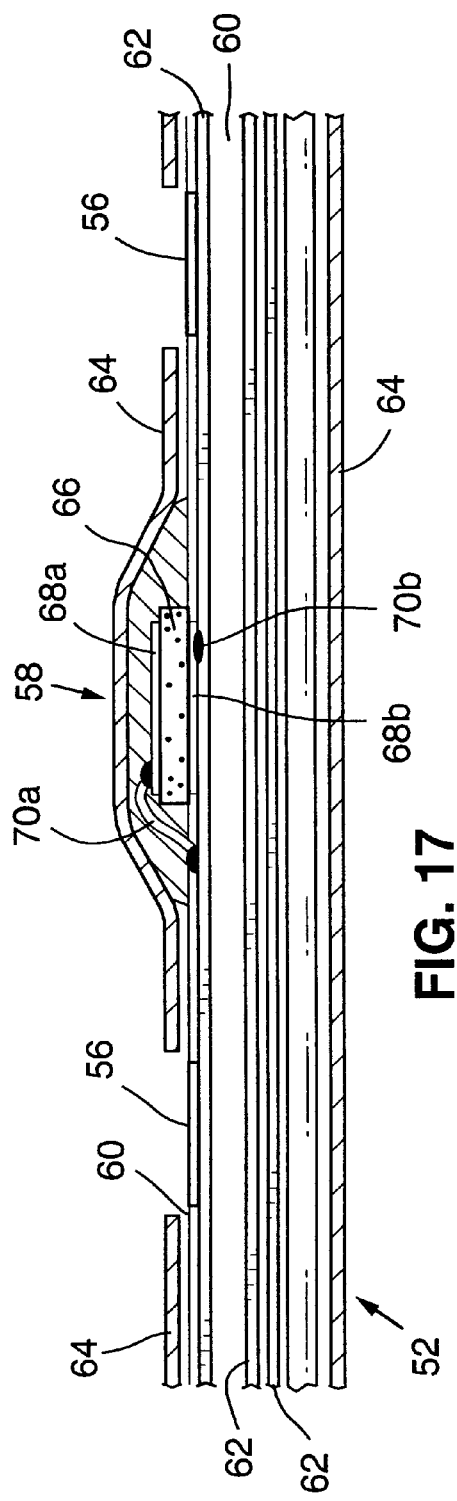

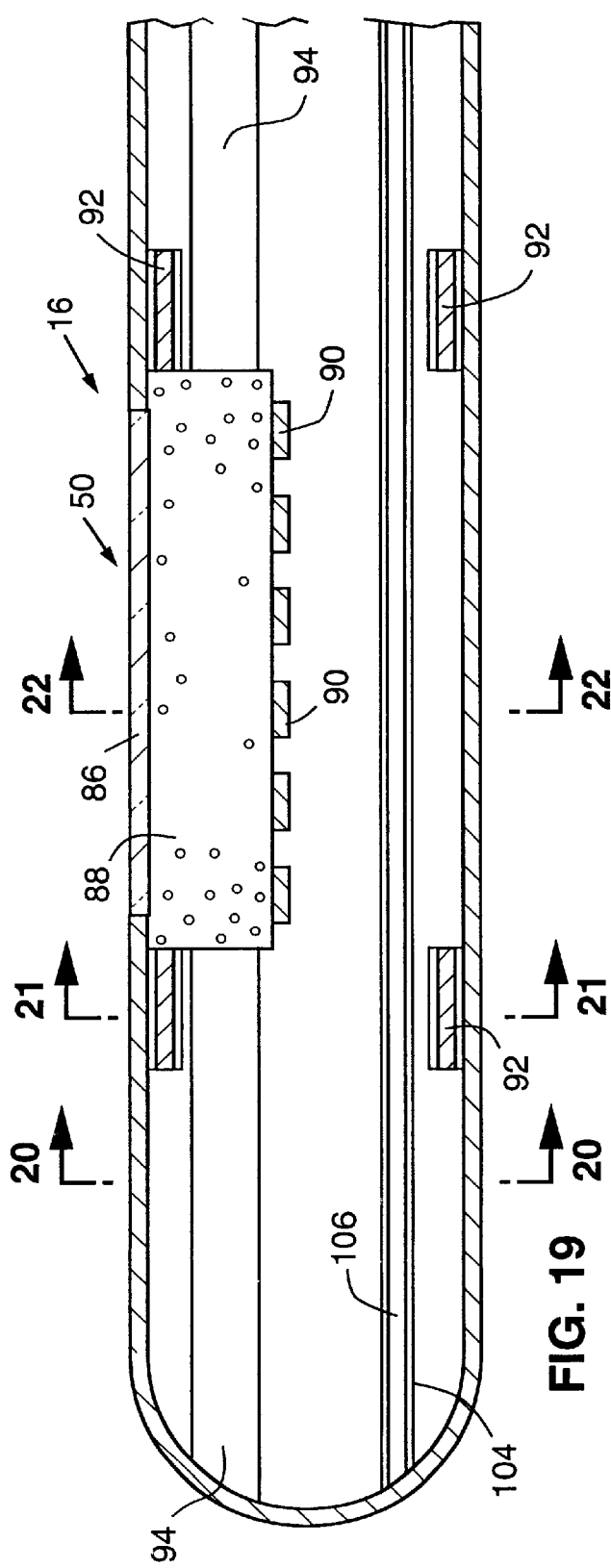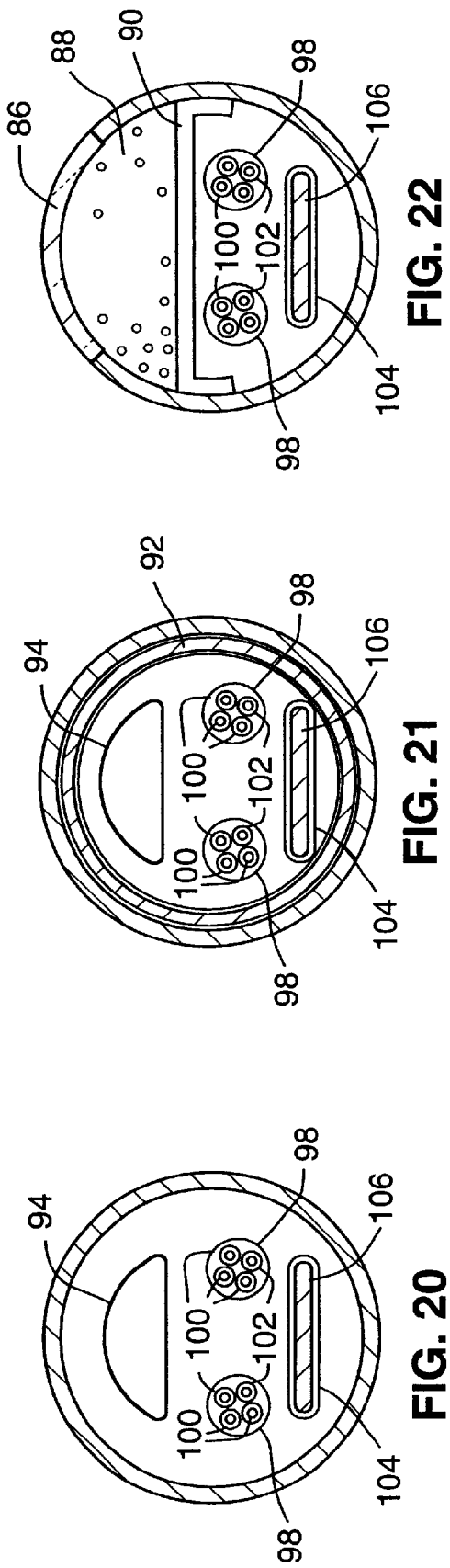
FIG. 19
FIG. 20
FIG. 21
FIG. 22

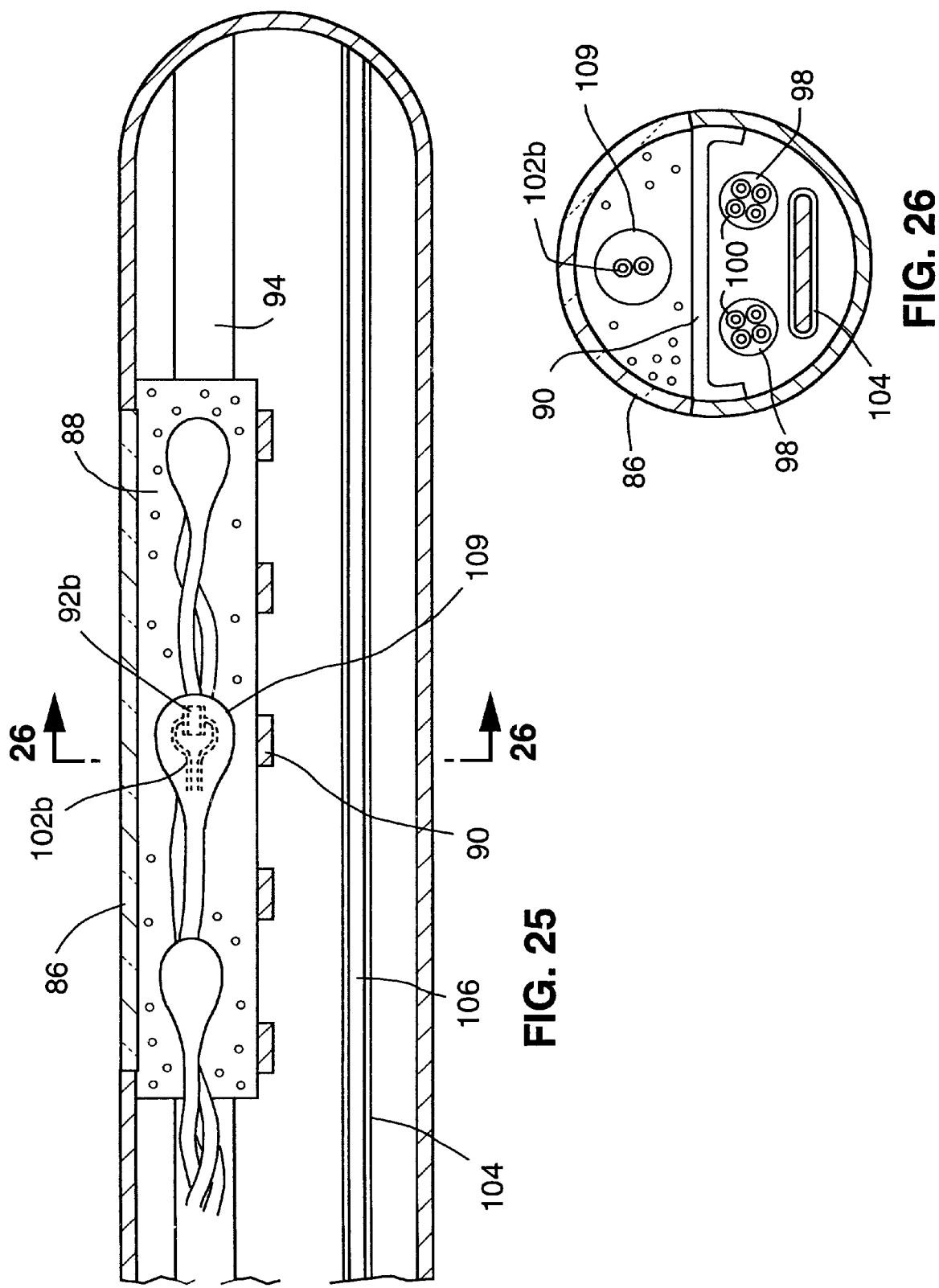

SYSTEM AND METHOD FOR ELECTRODE LOCALIZATION USING ULTRASOUND

FIELD OF THE INVENTION

The present invention relates generally to the field of ultrasound tracking systems. More specifically, it relates to systems for tracking the positions of devices within the human body.

BACKGROUND OF THE INVENTION

For certain types of minimally invasive medical procedures, endoscopic visualization of the treatment site within the body is unavailable or does not assist the clinician in guiding the needed medical devices to the treatment site.

Examples of such procedures are those used to diagnose and treat supra-ventricular tachycardia (SVT), atrial fibrillation (AF), atrial flutter (AFL) and ventricular tachycardia (VT). SVT, AFL, AF and VT are conditions in the heart which cause abnormal electrical signals to be generated in the endocardial tissue to cause irregular beating of the heart.

A procedure for diagnosing and treating SVT or VT involves measuring the electrical activity of the heart using an electrophysiology catheter introduced into the heart via the patient's vasculature. The catheter carries mapping electrodes which are positioned within the heart and used to measure electrical activity. The position of the catheter within the heart is ascertained using fluoroscopic images. A map of the measured activity is created based on the fluoroscopic images and is shown on a graphical display. A physician uses the map to identify the region of the endocardium which s/he believes to be the source of the abnormal electrical activity. An ablation catheter is then inserted through the patient's vasculature and into the heart where it is used to ablate the region identified by the physician.

To treat atrial fibrillation (AF), an ablation catheter is maneuvered into the right or left atrium where it is used to create elongated ablation lesions in the heart. These lesions are intended to stop the irregular beating of the heart by creating non-conductive barriers between regions of the atria. These barriers halt passage through the heart of the abnormal electrical activity generated by the endocardium. Following the ablation procedure, a mapping catheter is positioned in the heart where it is used to measure the electrical activity within the atria so that the physician may evaluate whether additional lesions are needed to form a sufficient line of block against passage of abnormal currents. S/he may also attempt to induce atrial fibrillation using a pacing electrode, and then further evaluate the line of block by analyzing the time required for the induced electrical activity to pass from one side of the block to the other.

The procedures used to diagnose and treat SVT, VT, AFL and AF utilize catheters which are maneuvered within the heart under fluoroscopy. Because the fluoroscopic image is in two-dimensions and has fairly poor resolution, it may be difficult for the physician to be certain of the catheter positions. Thus, for example, once a physician has identified an area which is to be ablated (using a map of the measured electrical activity of the heart) it may be difficult to navigate an ablation catheter to the appropriate location in order to accurately ablate the area of concern. It is therefore desirable to provide a system by which the positions of medical devices such as mapping and ablation catheters may be accurately guided to selected regions of the body.

Prior art tracking devices of the type which may track the positions of medical devices are described in U.S. Pat. No. 5,515,853 (Smith et al) and U.S. Pat. No. 5,546,951 (Ben Haim). While useful, neither of the disclosed systems provides for determining medical device locations relative to a fixed coordinate system within the body. The lack of a fixed coordinate system within the body can lead to tracking errors which in turn render it difficult to guide medical devices to the desired locations within the body.

It is therefore desirable to provide an ultrasound tracking system for medical devices which permits the tracking of devices relative to a fixed internal coordinate system. The system according to the present invention meets this objective as well as many others which enhance the accuracy and usefulness of the tracking system.

SUMMARY OF THE INVENTION

The present invention is a device localization system that uses one or more ultrasound reference catheters to establish a fixed three-dimensional coordinate system within a patient's heart, preferably using principles of triangulation. The coordinate system is represented graphically in three-dimensions on a video monitor and aids the clinician in guiding other medical devices, which also carry ultrasound transducers, through the body to locations at which they are needed to perform clinical procedures. In one embodiment of a system according to the present invention, the system is used in the heart to help the physician guide mapping catheters for measuring electrical activity, and ablation catheters for ablating selected regions of cardiac tissue, to desired locations within the heart.

Three-dimensional images are shown on a video display which represent the three-dimensional positions and orientations of at least portions of the medical devices used with the system, such as the reference catheter, and the electrodes of the mapping catheter and ablation catheter. The video display may additionally include representations of the electrical activity measured by each mapping electrode at its respective location on the three-dimensional display. It may also represent ablation lesions formed within the body at the appropriate three-dimensional locations, and/or certain anatomic structures which may facilitate navigation of the medical device(s) within the patient.

BRIEF DESCRIPTION OF THE DRAWINGS

FIG. 8 is a perspective view of a mandrel having a polymer piezoelectric wrapped around it for use with a reference catheter according to the present invention.

FIG. 9 is a side elevation view of a catheter for use with the system of the present invention which is provided with marking and ablation capabilities.

FIG. 10 is a perspective view of a first alternative embodiment of a catheter with marking and ablation capabilities according to the present invention.

FIG. 16 is a plan view of an arm of the mapping catheter of FIG. 13.

FIG. 17 is a cross-section view of the arm of FIG. 16, taken along the plane designated 17—17.

FIG. 19 is a side section view of the linear lesion catheter of FIG. 18.

FIG. 20 is a cross-section view taken along the plane designated 20—20 in FIG. 19.

FIG. 21 is a cross-section view taken along the plane designated 21—21 in FIG. 19.

FIG. 22 is a cross-section view taken along the plane designated. 22—22 in FIG. 19.

FIG. 25 is a side section view, similar to the view of FIG. 19, of an alternative embodiment of a linear lesion catheter for use with the system of the present invention.

FIG. 26 is a cross-section view taken along the plane designated 26—26 in FIG. 25.

FIG. 31 illustrates display of anatomical features, reference catheters, a linear lesion catheter, and burns formed in the heart using the linear lesion catheter. FIG. 32 illustrates display of the reference catheters, anatomical features, burns formed in the heart, and a basket catheter together with its mapping electrode positions.

FIG. 34A is an anterior section view of the heart showing placement of a reference catheter in the right ventricle and a marking catheter in the left ventricle. FIG. 34B is a lateral view of the heart showing a reference catheter in the coronary sinus. FIG. 34C is an anterior section view of the heart showing a reference catheter in the right ventricle and a mapping catheter in the left ventricle.

FIG. 36A is an anterior section view of the heart showing placement of a reference catheter in the RV apex and a marking catheter in left atria; FIG. 36B is an anterior section view of the heart showing a linear lesion ablation catheter in the left atria; FIG. 36C is an anterior section view of the heart showing a mapping catheter in the left atria.

DETAILED DESCRIPTION

Localization System Overview

The localization system and procedure will next be described in general terms. Specific examples of procedures which may be carried out using the system will be described in the Operation section of this description. The system is described primarily with respect to catheters in the heart, but it should be understood that the system is intended for use with other medical devices and in other regions of the body as well.

Figure 1:
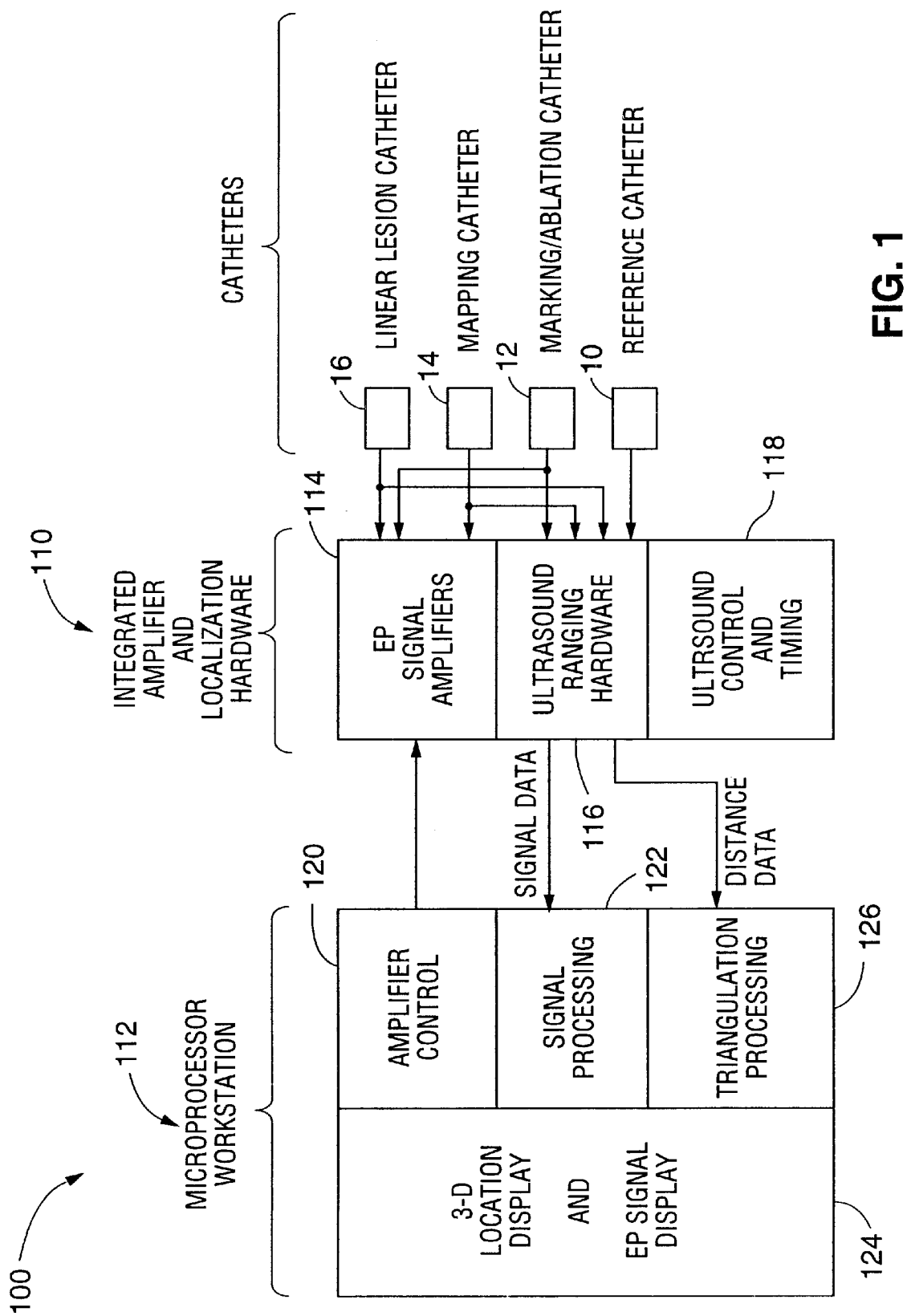
FIG. 1 is a schematic representation of the system according to the present invention, showing the major components of the system.

Referring to FIG. 1, the present invention is a device localization system 100 that uses one or more ultrasound reference catheters 10 to establish a three-dimensional coordinate system within a patient's heart. The system allows the positions of one or more additional catheters 12, 14, 16, to be represented graphically on a graphical user interface 124 relative to a coordinate system. This aids the clinician in guiding the additional catheters 12, 14, 16 through the heart to locations at which they are needed to perform clinical procedures.

In one embodiment of a system according to the present invention, the additional catheters include mapping catheters 14 for measuring electrical activity within the heart and ablation catheters 12, 16 for ablating selected regions of cardiac tissue. These catheters 12–16 may also be described as "electrophysiology catheters" or "EP catheters."

Each of the reference catheters 10 carries a plurality of ultrasound transducers, with there being a total of at least four such transducers employed during use of the system. The reference catheter transducers can function as ultrasound receivers by converting acoustic pressure to voltage, and as ultrasound transmitters by converting voltage to acoustic pressure. Each of the additional catheters 12, 14, 16 carries at least one ultrasound transducer which preferably functions as an ultrasound receiver but which may also function as a transmitter or a transmitter/receiver.

Using known techniques, the distance between each transducer and other ones of the transducers may be computed by measuring the respective time for an ultrasound pulse to travel from a transmitting transducer to each receiving transducer. These distance measurements are preferably carried out in parallel. In other words, when an ultrasound pulse is emitted by a reference catheter transducer, the system simultaneously measures the respective times it takes for the pulse to reach each of the other transducers being used in the system.

The velocity of an acoustic signal in the heart is approximately 1570–1580 mm/msec, with very small variations caused by blood and tissue. The time for an acoustic pulse to travel from one transducer to another may therefore be converted to the distance between the transducers by multiplying the time of flight by the velocity of an acoustic pulse in the heart (i.e. by 1570–1580 mm/msec). As detailed below, the system of the present invention uses this "time of flight" principal in combination with the geometric principal of triangulation to establish a three-dimensional coordinate system using the reference transducers on the reference catheter 10, and to then use the additional catheter transducers to track the location of an additional catheter 12, 14, 16, relative to the coordinate system.

During use of the system of the invention, one or more of the reference catheters 10 is introduced into the heart or the surrounding vasculature (or even into other areas such as the esophagus) and is left in place for the duration of the procedure. Once reference catheter(s) 10 are positioned within or near a patient's heart, the system first measures the distances between each of the reference catheter transducers using the "time of flight" principal. It then uses these distances to establish the relative positions of the reference transducers and therefore to establish a three-dimensional coordinate system.

Figure 2:
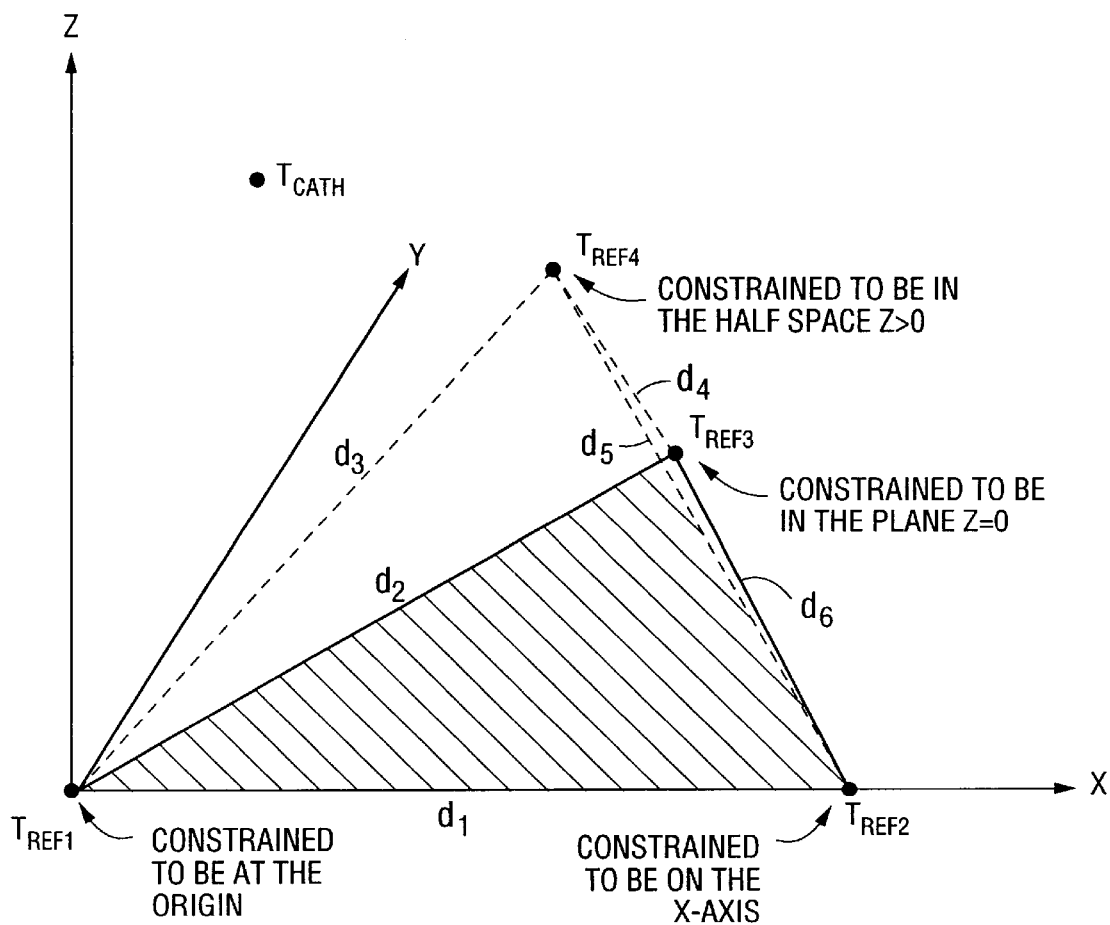
FIG. 2 is a schematic representation of a three-dimensional coordinate system established using a reference catheter according to the present invention.

Referring to FIG. 2, establishing the coordinate system requires placement of the reference catheter(s) 10 such that at least four reference transducers, designated $T_{REF1}$ through $T_{REF4}$ in FIG. 2, are available to define a 3-dimensional coordinate system as follows: $T_{REF1}$ through $T_{REF3}$, define the plane P at z=0; one reference transducer $T_{REF1}$ defines the origin of the coordinate system; a line between $T_{REF3}$ and $T_{REF2}$ defines the x-axis of the system; and $T_{REF3}$ lies in the plane z=0. The fourth reference transducer, $T_{REF4}$, lies on one side of the plane P, at z>0. Given these constraints, the coordinates of the reference transducers can be computed using the law of cosines. See, for example, Advanced Mathematics, A preparation for calculus, 2nd Ed., Coxford, A. F., Payne J. N., Harcort Brace Jovanovich, New York, 1978, p. 160.

Each of the reference transducers $T_{REF1}$ through $T_{REF4}$ must be capable of both receiving and transmitting ultrasound pulses. As discussed, each reference transducer is separately made to emit acoustic pulses that are received by each of the other reference transducers so that the distances d1 through d6 shown in FIG. 2 are calculated using the respective times it takes for an acoustic pulse to travel between each pair of the reference transducers. These distances are triangulated to establish the positions of the reference transducers relative to each other, and therefore to establish a three-dimensional coordinate system.

Once a 3-dimensional coordinate system is established in the manner described, the three-dimensional location of an additional catheter transducer placed near or within the heart (such as a transducer on a mapping or ablation catheter 12, 14, or 16) can be calculated as follows. First, using the "time of flight" method, the distances between each of the reference transducers $T_{REF1}$ through $T_{REF4}$ and the additional catheter transducer (designated $T_{CATH}$ in FIG. 2) are established, in parallel. In practice, these distances are preferably also performed in parallel with the distance measurements that are made to establish the coordinate system. Next, using basic algebra and the law of cosines (see, e.g., the Advanced Mathematics text cited above), the coordinates of $T_{CATH}$ relative to the reference transducers are calculated using the measured distances from $T_{REF1}$ through $T_{REF4}$ to $T_{CATH}$. This process is referred to as triangulation.

The locations of all or portions of the reference catheters may be displayed as well. The system is preferably programmed to extrapolate catheter position from the coordinates of the transducer locations based on models of the various catheters pre-programmed into the system, and to display each catheter's position and orientation on a graphical user display (see display 124 in FIG. 1). The locations of all or portions of the additional catheters (such as, for example, their distal tips, their electrodes or ablation sections, if any, or other sections which may be of interest) are displayed.

The reference catheter(s) 10 thereby establish an internal coordinate system by which the relative positions of EP catheter transducers in the heart may be calculated using triangulation and shown in real-time on a three dimensional display.

Ultrasound Catheters

Figure 18:
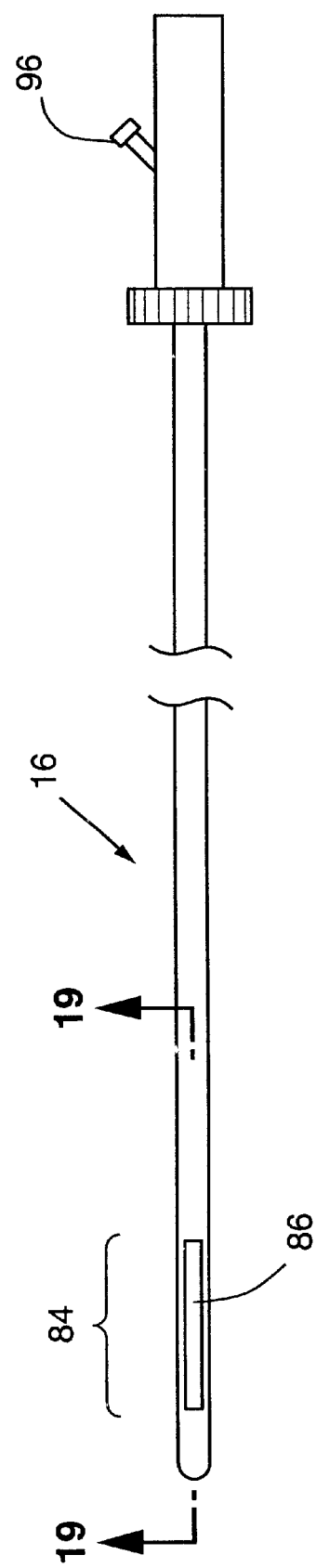
FIG. 18 is a side elevation view of a linear lesion catheter for use in the system according to the present invention.

Catheters of the type which may be used with the system according to the present invention are shown in FIGS. 3, 9, 13 and 18. These include a reference catheter 10 (FIG. 2), a marking and ablation catheter 12 (FIG. 9), a basket-type mapping catheter 14 (FIG. 13), and a linear lesion ablation catheter 16 (FIG. 18).

Reference Catheters

Figure 3:
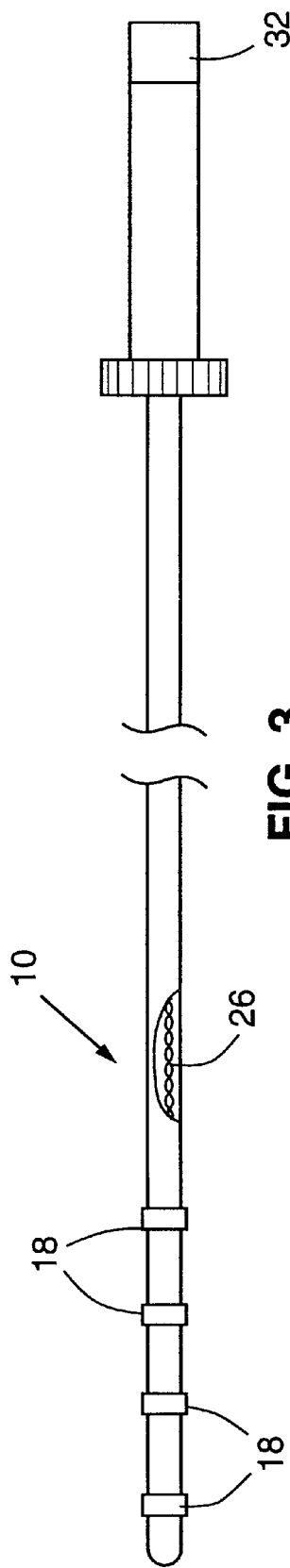
FIG. 3 is a side elevation view of a reference catheter for use with the system according to the present invention.

Referring to FIG. 3, a reference catheter according to the present invention is an elongate catheter having a plurality of ultrasound transducers 18 positioned at its distal end. The transducers 18 are piezoelectric transducers capable of transmitting and receiving ultrasound signals.

The reference catheters can be integrated with typical EP catheters by providing the ultrasound transducers described above. This allows the system to utilize the localization function using catheters which are already needed for the EP procedure. Thus, use of the system does not require the physician to use more catheters than would be used had the EP procedure been carried out without the localization function.

Figure 4:
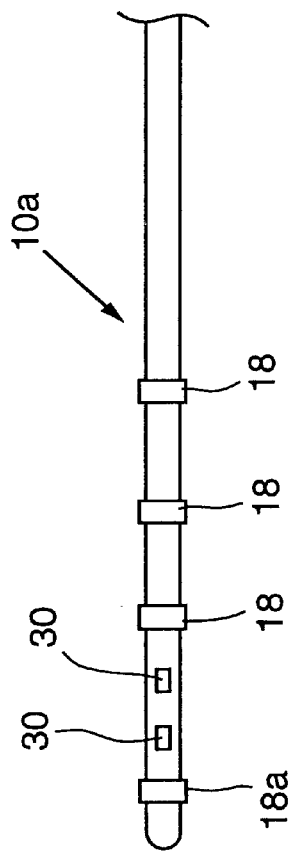
FIG. 4 is a side elevation view of a first alternative embodiment of a reference catheter for use with the system according to the present invention, in which ultrasound transducers are included on a catheter of a type conventionally used in the RV apex.
Figure 5:
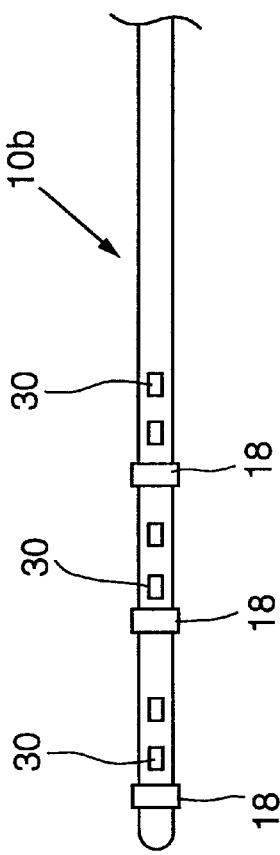
FIG. 5 is a side elevation view of a second alternative embodiment of a reference catheter for use with the system according to the present invention, in which ultrasound transducers are included on a catheter of a type conventionally used in the coronary sinus.

For example, referring to FIG. 4, the reference catheter 10a may be an RV apex catheter having a distal pair of EP electrodes 30, an ultrasound transducer 18a at the distal tip, and additional ultrasound transducers 18 proximally of the distal tip. It may also be a coronary sinus reference catheter 10b (FIG. 5) having at least three bipole pairs of EP electrodes 30 distributed over the section of the catheter that is positioned in the coronary sinus, and having at least three ultrasound transducers also distributed over the section of the catheter that is in the coronary sinus.

Figure 6:
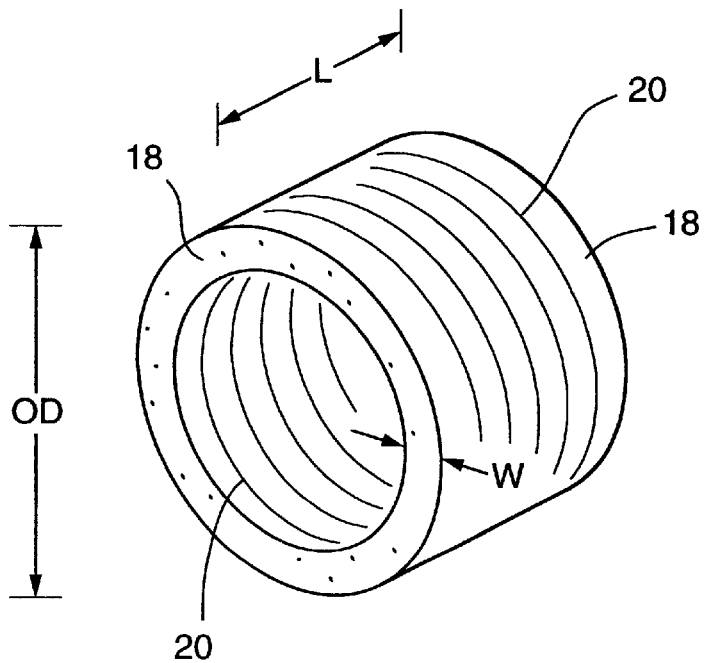
FIG. 6 is a perspective view of a piezoelectric cylinder of a type which may be used on catheters according to the present invention, including those shown in FIGS. 3–5.

Referring to FIG. 6, a preferred transducer 18 is a piezoelectric cylindrical tube having inner and outer surfaces. The cylindrical transducer may be made of PZT-5H, PZT-5A, PMN (lead metaniobate or lead magnesium niobate) or other piezoelectric ceramic materials.

Electrodes 20 are positioned on the inner and outer surfaces of the transducer. The electrodes are metal surfaces not limited to materials such as sputtered chrome and gold, electroless nickel, or fired silver. The piezoelectric ceramic is polarized in the thickness mode, i.e., between the two electrodes 20.

The cylinder includes an outside diameter (designated "OD" in FIG. 6) of approximately 0.040 to 0.250 inches, and preferably approximately 0.060 to 0.090 inches. The cylinder has a length L of approximately 0.020 to 0.125 inches and preferably approximately 0.030 to 0.060 inches. Wall thickness W is approximately 0.004 to 0.030 inches and preferably approximately 0.006 inches to 0.015 inches. The transducers 18 are spaced from one another along the catheter 20 (FIG. 3) by a distance of approximately 0.5–10 cm, and most preferably 1–3 cm.

Preferably, the localization system is operated using the same operating frequencies for all transducers. The optimal operating frequency for the system is determined by considering the resonant frequencies of the ultrasound transducers used for the catheters in the system. It has been found that, given the dimensions and thus the resonances of the preferred transducers being used in the system, the transducers are most preferably operated at a frequency of approximately 1.0–3.0 MHz, which in the case of the transducer 18 is the transducer resonance in the length mode. Transducer 18 further has a beam width of approximately 114°, where the beam width is defined as the angle over which the signal amplitude does not drop below 6 dB from the peak amplitude. If desired, a diverging lens 22 (FIG. 7), in the form of a spherical bead of epoxy or other material may be formed over the ceramic cylinder to make the signal strength more uniform over the beam width.

Referring to FIG. 8, the reference catheter transducers 18b may alternatively be formed of piezoelectric polymer films of copolymers such as PVDF. Such films would have thicknesses of approximately 0.005–1.0 mm, and preferably approximately 0.007–0.100 mm, and would preferably include gold film electrodes on the inner and outer surfaces. As shown in FIG. 8, the polymer film would be wrapped around a mandrel 24 (which may be part of the catheter shaft 10c itself or a separate polymer plug inside the catheter 10). A transducer configuration of this type operates with a very large band width and does not have a specific resonance due to the polymer piezoelectric.

Electrode leads (not shown) are attached to the inner and outer transducer electrodes (such as electrodes 20 of FIG. 6).

Figure 7:
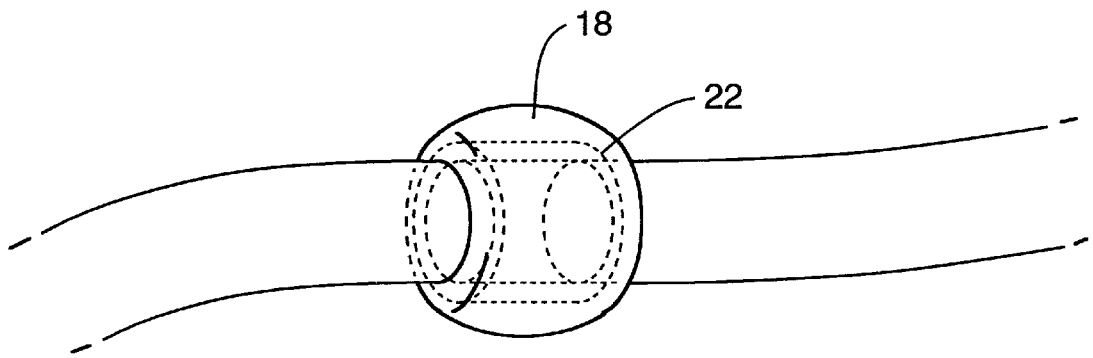
FIG. 7 is a side elevation view of the piezoelectric cylinder of FIG. 6 mounted on a catheter and modified to include a divergent lens.

If piezoelectric ceramics are used as in FIGS. 6 and 7, leads may be attached using low temperature solders which typically contain large proportions of indium metal. Leads may alternatively be attached with silver epoxy. It is important that the leads be attached using a minimum amount of material to minimize distortion of the acoustic field. In the case of the polymer transducers of FIG. 8, photo lithographic techniques are typically used to create electrodes and their associated lead tabs. In this manner, the one side electroded polymer at the tab site does not contribute to the acoustic field. Leads are typically attached to these tabs with either low temperature indium based solders or with silver epoxy. Therefore, for these polymer transducers, the amount of material on the connection tab does not affect the acoustic field.

The reference catheter preferably includes at least four such transducers so that a three-dimensional coordinate system can be established using a single catheter. If desired, the reference catheter may have more transducers or it may have fewer transducers if more than one reference catheter is to be used to establish the three-dimensional coordinate system. Using more than four reference transducers is advantageous in that it adds redundancy to the system and thus enhances the accuracy of the system. When more than four reference transducers are used, the problem of determining the location of catheter transducers is over determined. The additional redundancy may provide greater accuracy if the measured distances between the reference transducers and catheter transducers are noisy. The overdetermined problem can be solved using multi-dimensional scaling as described in "Use of Sonomicrometry and Multidimensional Scaling to Determine 3D Coordinates of Multiple Cardiac Locations: feasibility and implementation", Ratciffle et. al, IEEE Transactions Biomedical Engineering, Vol. 42, no. 6, June 1995.

Referring again to FIG. 3, a connector 32 enables the catheter 10 to be electrically coupled to the ultrasound ranging hardware 116 (described below and shown in FIG. 1).

Four twisted pairs 26 of Teflon coated forty-two gauge copper wire (one pair can be seen in the cutout section shown in FIG. 3) extend from connector 32 through the catheter 10. Each twisted pair 26 is electrically coupled to a corresponding one of the ultrasound transducers 18, with one wire from each pair 26 coupled to one of the transducer electrodes 20 (FIG. 6). When a transducer is to act as an ultrasound transmitter, a high voltage pulse (i.e, approximately 10–200V) is applied across the corresponding twisted pair 21 and causes the transducer 18 to generate an ultrasound pulse. When a transducer is to act as an ultrasound receiver, the ultrasound ranging hardware 116 (FIGS. 27A–27B, described below) awaits receive pulses of approximately 0.01–100 mV across the twisted pairs corresponding to receiving transducers. Additional leads (not shown) couple the EP electrodes 30 to the EP hardware 114 (FIG. 1).

To facilitate manipulation of the reference catheter through a patient's vessels and into the heart, the reference catheter 10 may have a pre-shaped (e.g. curved) distal end.

Marking/Ablation Catheter

Referring to FIG. 9, the system of the present invention preferably utilizes a catheter 12 to identify the locations of anatomical landmarks (such as the septal wall) relative to the coordinate system so that the landmarks may be included on the three-dimensional display. Showing anatomical landmarks on the display correlates the three-dimensional coordinate system to discrete anatomical locations and thereby assists the physician in navigating EP catheters to the desired locations within the heart.

The marking catheter 12 is preferably a 7 French steerable catheter having one or more ultrasound transducer(s) 34 mounted at or near its distal tip. Preferably, the catheter 12 includes one transducer at or near its distal tip and a second transducer spaced from the distal tip by approximately 0.5–4.0 cm. The marking catheter 12 need not be one which is limited to use in marking anatomical sites. It can be a catheter useful for other purposes as well; the term "marking catheter" is being used in this description as a matter of convenience. Catheter 12 may also include an ablation electrode 36 at its distal tip, so that it may also be used to ablate tissue while the position of the ablation electrode 36 is tracked using the localization system 100. It may also include other electrophysiology electrodes 38 which may be used for pacing and/or mapping as desired by the user.

The transducers 34 may be similar to the reference catheter transducers 18. While the outer diameter and wall thickness of the transducers 34 may differ from that of transducer 18 to accommodate mounting requirements, the length of the transducers 34 is preferably the same as that of the transducers 18 to assure a common operating frequency of approximately 1.0–3.0 MHZ.

Figure 11:
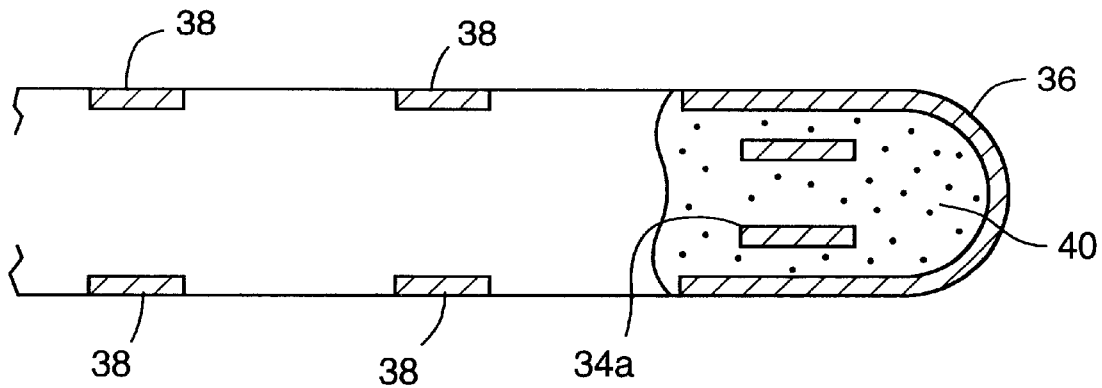
FIGS. 11 and 12 are side section views of second and third alternative embodiments of catheters having marking and ablation capabilities according to the present invention.
Figure 12:
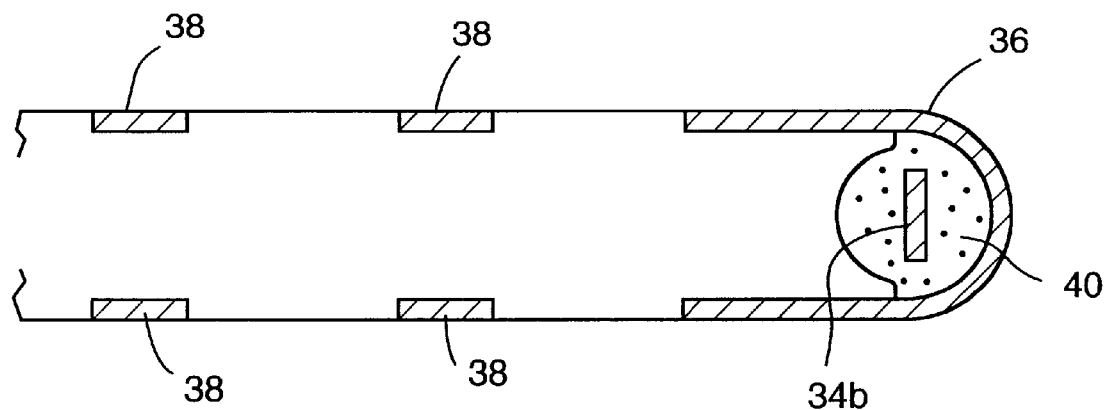

Alternatively, the more distal transducer might be packaged differently than the reference catheter transducers. For example, referring to FIG. 10, the transducer 34 may be mounted just proximal of the distal ablation tip 36. Alternatively, a cylindrical transducer 34a or a plate transducer 34b may be positioned inside the distal ablation tip, in FIGS. 11 and 12, respectively. An internal piezoelectric transducer would be embedded in a bead of epoxy 40 positioned in the catheter tip. This bead would preferably have a spherical contour across the distal end so that it would act as a divergent lens for the ultrasound energy. The metal forming the ablation tip 36 must be very thin (i.e., less than a small fraction of a wavelength) to facilitate the transmission of acoustic energy to and from an internal transducer.

The marking catheter 12 may additionally be provided with EP electrodes 38. As shown in FIG. 9, a handle 42 and a knob 44 for actuating a pull wire (not shown) allow the marking catheter 12 to be maneuvered through a patient's vessels and heart using conventional steering mechanisms. A connector 46 enables the catheter 12 to be electrically coupled to the EP hardware 114 and the ultrasound ranging hardware 116 (described below, see FIG. 1).

Mapping Catheter

Figure 13:
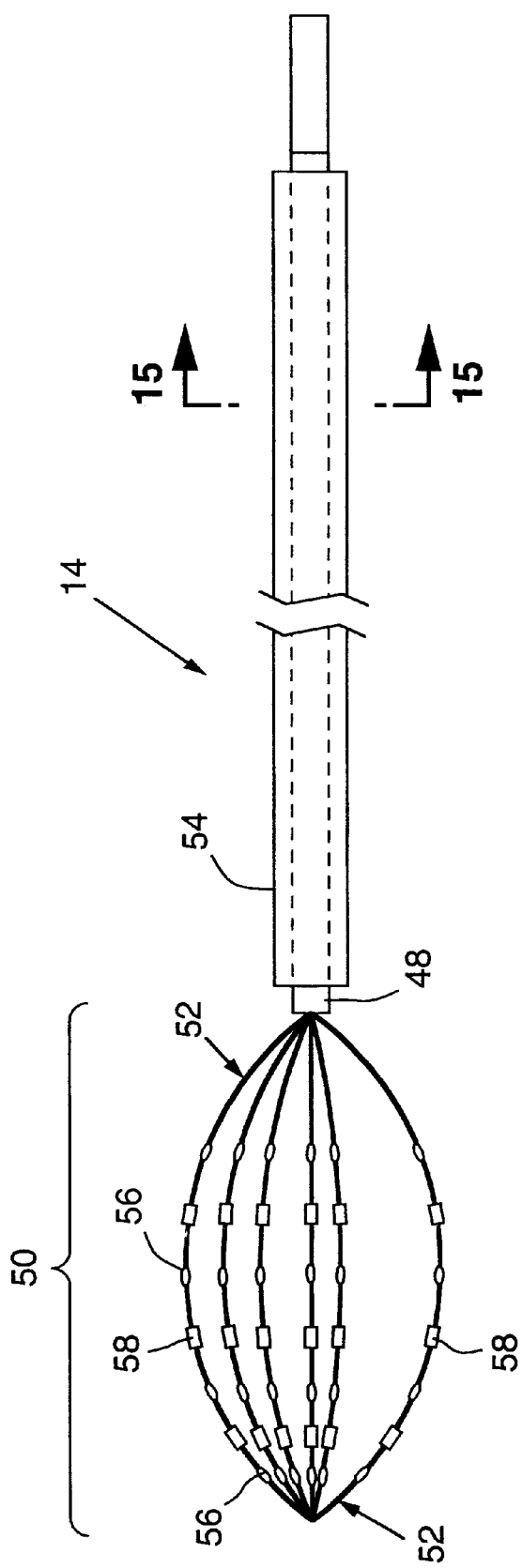
FIG. 13 is a side elevation view of a mapping catheter for use with the system of the present invention. As with all of the catheters shown herein, the sizes of the electrodes and transducers are exaggerated for purposes of illustration.

FIG. 13 shows a first embodiment of a mapping catheter 14 for use with the system according to the present invention. The catheter 14 is of the type known in the art as a "basket" catheter. It includes an elongate shaft 48 carrying a mapping basket 50 at its distal end. The basket 50 is formed of preferably eight arms 52. Arms 52 are constructed of ribbons of a shape memory material such as Nitinol. The shape memory material is treated such that the ribbons assume the basket structure shown in FIG. 13 when in an unstressed condition.

Figure 14A:
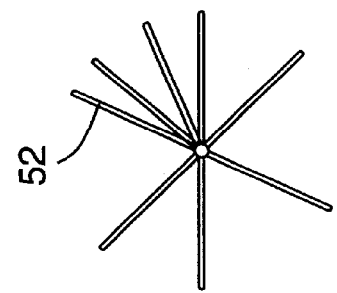
FIG. 14A is a front elevation view of the mapping catheter of FIG. 13, showing the spacing of the basket arms.
Figure 14B:
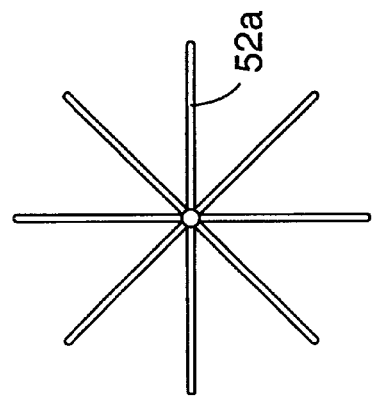
FIG. 14B is a view similar to the view of FIG. 14A showing alternate basket arm spacing.

The arms 52 may be concentrated at one section of the basket (FIG. 14A) so that during use mapping may be concentrated in one area of a cardiac chamber. The arms may alternatively be uniformly spaced as shown in FIG. 14B. Basket catheters of these types are shown and described in U.S. Pat. No. 5,156,151, the disclosure of which is incorporated herein by reference.

A sheath 54 is disposed around shaft 48. Sheath 54 is longitudinally slidable between the proximal position in FIG. 13 and a distal position in which the basket 50 is compressed within it. During use the sheath 54 is moved to the distal position to compress the basket before the catheter 14 is inserted into the patient, so that the basket can be easily moved through the patient's vessels and into the patient's heart. Once the basket is within the desired chamber of the patient's heart, the sheath is withdrawn, the basket is opened into its expanded condition, (either by spring action of the arms 52 or by a separate actuator) and the arms to map electrical activity of the chamber wall.

Each arm 52 of the basket catheter 14 carries a plurality of EP mapping electrodes 56 designed to detect the electrical activity of underlying cardiac tissue. A plurality of ultrasound receiving transducers 58 are also mounted to each arm 52. Preferably, the mapping electrodes 56 and the ultrasound transducers 58 alternate with each other along the length of each arm 52, although there need not be one-to-one correspondence between the transducers and electrodes.

FIG. 16 is a plan view of one arm 52 of basket catheter 14, and FIG. 17 is a side section view of the arm of FIG. 16. As shown, the mapping electrodes 56 and ultrasound transducers 58 are preferably formed on a flex circuit 60 which is attached to the arm 52. Copper leads 62 are formed on the flex circuit and each lead is electrically connected to one of the EP electrodes 56 and one of the ultrasound transducers 58, and to the EP and localization hardware 110 (FIG. 1). Each arm 52, including its associated flex circuit 60, is covered in polyethylene shrink tubing 64, with only the electrodes 56 being exposed through the shrink tubing 64.

Referring to FIG. 16, a preferred piezoelectric transducer for the mapping catheter comprises a flat piezoelectric ceramic plate 66. The plate 66 may be made of PZT-5H, PZT-5A, PMN (lead metaniobate or lead magnesium niobate) or other piezoelectric materials.

The transducer includes a depth D and length L, each of approximately 0.010 to 0.060 inches, and preferably approximately 0.025 to 0.040 inches. The transducer has a wall thickness W of approximately 0.004 to 0.030 inches and preferably approximately 0.006 to 0.015 inches. The length and depth resonances of the transducer fall in the range from 1.0 MHz to 3 MHz and thus contribute to the overall performance of the system. The beam width considerations are the same as those described above for the reference catheter transducers 18 (FIG. 6).

Electrodes 68a, 68b are positioned on the upper and lower flat surfaces of the plate. The electrodes are metal surfaces not limited to materials such as sputtered chrome and gold, electroless nickel, or fired silver. The piezoelectric ceramic is polarized in the thickness mode, i.e., between the two electrodes.

The mapping catheter transducers 58 may alternatively be formed of piezoelectric polymer films of copolymers such as PVDF. Such films would have thicknesses of approximately 0.005–1.0 mm, and preferably approximately 0.007–0.100 mm, and would preferably include gold film electrodes on the inner and outer surfaces. The polymer film would preferably be taped to the printed wiring board of the basket arm, and leads attached to the top electrodes in a manner similar to that mentioned above for the reference catheter transducers. Alternatively, the polymer film could be used to form the entire flex circuit.

Lead wires 70a, 70b extend between the copper leads 62 and the electrodes 68a, 68b. It is important to note that each of the leads 62 electrically connects both an ultrasound transducer 58 and an EP electrode 56 to the EP and localization hardware 110. Each lead 62 therefore carries electrical activity measured by EP electrodes 56 as well as receive signals from the ultrasound transducers 58 to the hardware 110. It is possible to do this because EP signals have a lower frequency (i.e., on the order of 1 Hz–3 kHz) than the ultrasonic signals, which have frequencies of approximately 500 kHz–30 MHz. Thus, the EP signals can be removed from the recorded signal using low-pass filtering while the ultrasound signal can be removed using high pass filtering.

Combining EP and ultrasound signals on the same lead 62 has the advantage of reducing the total number of conductors in the catheter 14. While this is advantageous, it is not a requirement for functionality of the system. Naturally, the system may also be provided using separate leads for the EP and ultrasound signals.

For both piezoelectric ceramic and polymer transducers, one lead 70b will most typically be attached by bonding the bottom electrode 68b of the piezoelectric (e.g., plate 66) with silver epoxy to the printed circuit of the basket arm. Leads 70a may be attached to the top electrodes 68a in a manner similar to that set forth with respect to the reference catheter transducers. For the piezoelectric ceramics 66, the top lead 70a may be attached with low temperature solders which typically contain large proportions of indium metal. It is important that the leads be attached using a minimum amount of material to minimize distortion of the acoustic field. Top leads 70a may also be attached with silver epoxy. In the case of the polymer piezoelectrics, metallization of the electrodes and leads is typically achieved using photo lithographic techniques. In this manner, the one side electroded polymer at the lead site does not contribute to the acoustic field as discussed previously for the polymer transducer of the reference catheter.

Acoustic wave propagation does not occur across a vacuum or air gap, consequently it is necessary to provide a rubber path or a path through an insulating polymer in order to fill air gaps around the transducers. For example, after the top lead 70a has been attached, the entire top surface and surrounding areas including the inner surface of the shrink tubing is coated with a rubber primer. Subsequently, the area between and around the top surface of the piezoelectric and the shrink tubing is filled with a silicone rubber material.

Alternatively, the top surface of the piezoelectric and the electrical lead may be coated with an insulating polymer. After the heat shrink tubing is attached to the basket strut, a small area over and around the top electrode of the ceramic may be cut out of the shrink tubing to provide an unobstructed exposure of the transducer to the blood field.

The EP electrodes 56 are preferably platinum black electrodes having a size of approximately 0.009×0.030 inches. For these small electrodes, platinum black is used for low impedance, i.e., approximately less than 5.0 k Ohms over the frequency range (approximately 1 Hz–3 kHz) of interest for EP signals. This is important in that it prevents the impedance of the ultrasound transducers from loading the output of the EP electrodes.

Figure 15:
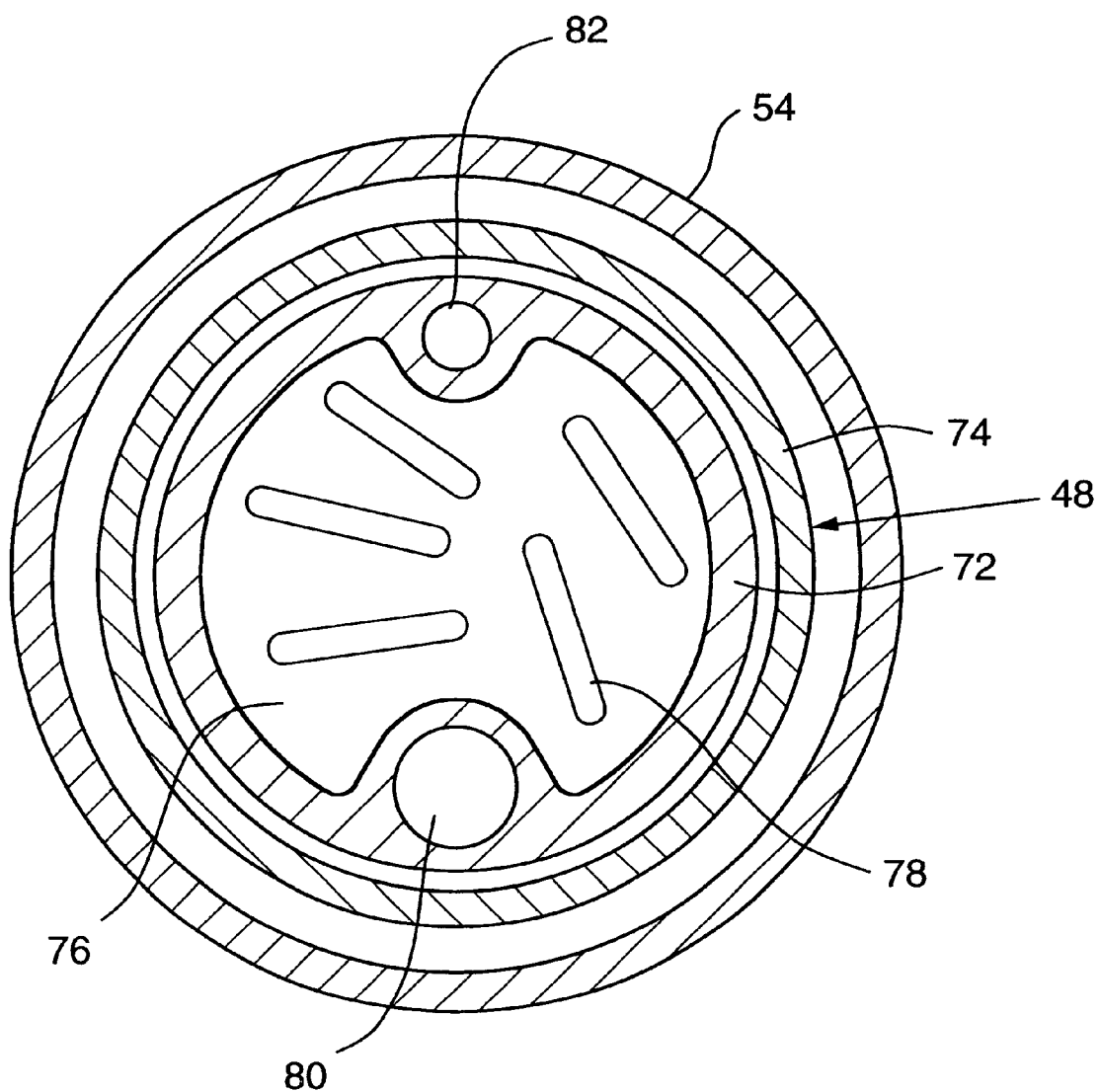
FIG. 15 is a cross-section view of the mapping catheter taken along the plane designated 15—15 in FIG. 13.

FIG. 15 is a cross-section view of the portion of the catheter 14 which is proximal of the basket 50. The catheter shaft 48 is formed of an inner shaft 72 and an outer, braided shaft 74 preferably made from stainless steel braid of a type conventionally known in the art. The inclusion of the braid improves the torque characteristics of the shaft 48 and thus makes the shaft 48 easier to maneuver through patient's vessels and heart.

Inner shaft 72 includes a center lumen 76 through which ribbon cables 78 extend. Leads (not shown) are formed on the ribbon cables 78 and function to carry signals corresponding to signals received by the ultrasound transducers 58 and by the electrophysiology electrodes 56 to the system hardware 110 (FIG. 1). An ablation catheter lumen 80 extends through the shaft 48 and allows an ablation catheter such as catheter 12 to be introduced through the shaft 48 and into contact with tissue surrounding the basket 50.

Inner shaft 72 further includes a deflection lumen 82. A pull wire (not shown) extends through the deflection lumen 82 and facilitates steering of the basket using means that are conventional in the art.

Linear Lesion Ablation Catheter

FIGS. 18 through 26 show a linear lesion ablation catheter 16 for use with the system 100 of the present invention. Catheter 16 is an elongate shaft preferably constructed of a thermoplastic polymer, polyamid ether, polyurethane or other material having similar properties. An ablation section 84, the section of the catheter 16 at which ablation is carried out, is located at the distal end of the shaft.

As shown in FIG. 18, an elongate window 86 is formed in the wall of the ablation section 84. The window 86 may be made from heat shrink polyethylene, silicone, or other polymeric material having a plurality of small holes or perforations formed in it. It may alternatively be formed of the same material as the remainder of the shaft and simply include a plurality of holes formed through it.

Referring to FIG. 19, a foam block 88 is disposed within the catheter, next to the window 86. The foam block 88 is formed of open cell polyurethane, cotton-like material, open-cell sponge, hydrogels, or other foam-like materials or materials that are permeable by conductive fluids. A plurality of RF ablation electrodes 90 line the edge of the foam block 88 such that the foam block lies between the electrodes 90 and the window 86.

Ultrasound transducers 92 are positioned at the distal and proximal ends of the foam block 88. The transducers 92 are preferably formed of piezoelectric ceramic rings having electrodes bonded to their inner and outer surfaces, although the transducers may also be formed in a variety of alternative shapes.

Referring to FIGS. 20–22, several lumen extend through the catheter 16. The first is a fluid lumen 94 that extends the length of the catheter 16 and is fluidly coupled to a fluid port 96 (FIG. 18) at the proximal end of the catheter. It should be noted, with reference to FIG. 20, that the walls of the fluid lumen are cut away at the ablation section 84 to accommodate placement of the foam block 88 and the RF electrodes 90 within the catheter.

A pair of lead lumen 98 house lead wires 100 that carry RF energy to the electrodes 90 and lead wires 102 that carry voltage signals from the transducers 92. A fourth lumen 104 houses a Nitinol core wire 106 which provides rigidity to the catheter.

Because breaks in a linear lesion can reduce the success of an ablation procedure by leaving a path through which current may travel during atrial fibrillation episodes, the fluid lumen, foam, and window are provided to improve the coupling of the RF energy to the cardiac tissue to minimize the likelihood of breaks in the lesion.

Specifically, during use, the window 86 of ablation section 84 of the apparatus is positioned adjacent to the body tissue that is to be ablated. RF energy is delivered to the electrodes 90 while saline or other conductive fluid is simultaneously delivered through the fluid lumen 94. The conductive fluid passes out of the fluid lumen 94 and into the foam 88, and contacts the electrodes 90. The fluid also flows through the window 86 into contact with the body tissue, thereby improving the coupling of the RF energy from the electrodes 90 to the tissue and improving the efficiency of the ablation of the tissue.

Using a conductive liquid dispersed over the desired area as a mechanism for coupling RF energy to the tissue produces lesions having greater continuity (and thus fewer breaks through which current can pass during atrial fibrillation episodes) than lesions formed by apparatuses that rely solely on direct contact between the electrodes and the body tissues, decreasing the likelihood of thrombus formation on the electrodes and thus decreasing the chance of an embolism. The foam and the window improve ablation in that the conductive liquid is uniformly dispersed within the foam and then is focused onto the body tissue as it passes through the holes or pores in the window. This concept, and several alternate ways of configuring linear lesion catheters that may be adapted to include ultrasound transducers and used in the system of the present invention, are described in published International Application PCT/US96/17536, the disclosure of which is incorporated herein by reference.

Figure 23:
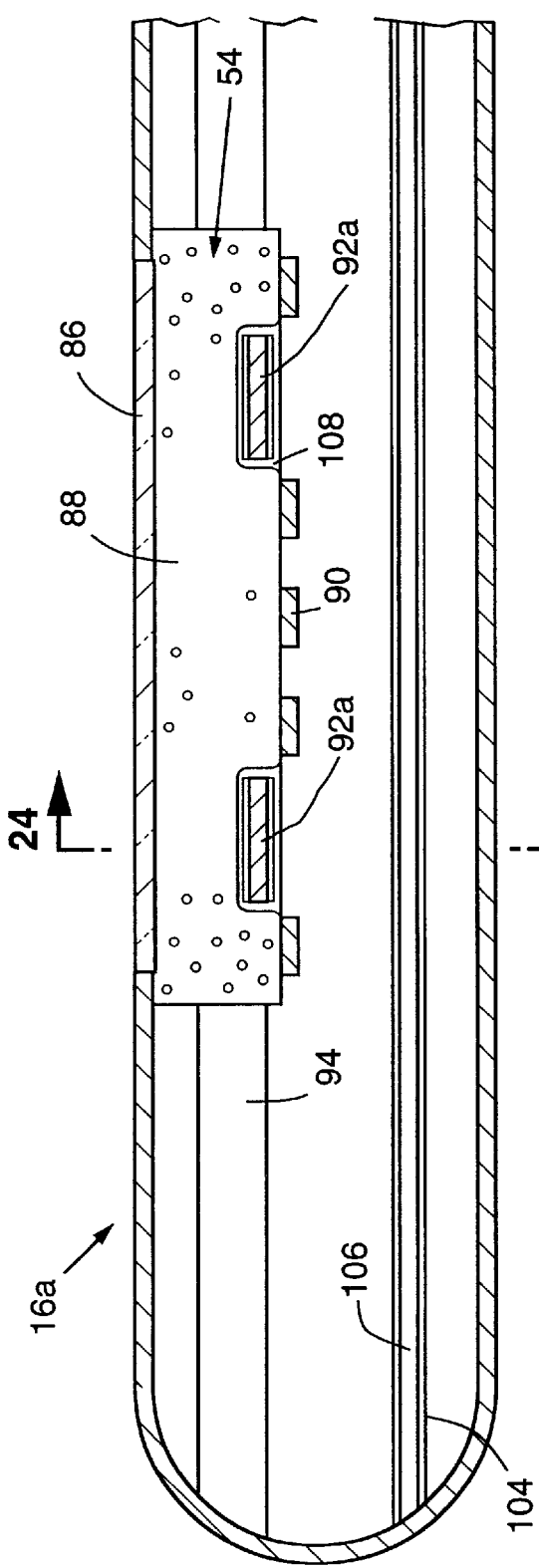
FIG. 23 is a side section view, similar to the view of FIG. 19, of an alternative embodiment of a linear lesion catheter for use with the system of the present invention.
Figure 24:
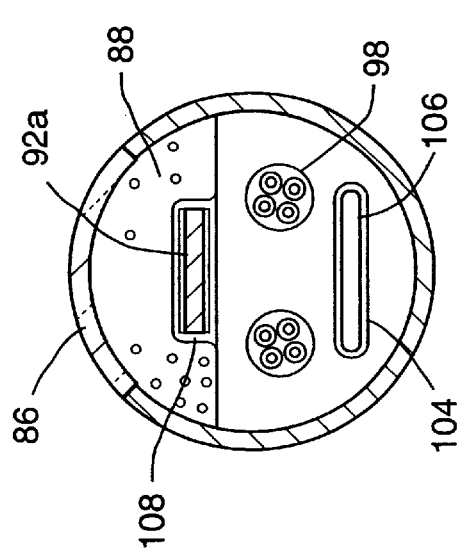
FIG. 24 is a cross-section view taken along the plane designated 24—24 in FIG. 23.

FIGS. 23 and 24 show a first alternative embodiment of a linear lesion catheter according to the present invention. The first alternative embodiment 16a differs from the embodiment of FIG. 19 primarily in the shape and placement of the transducers. Transducers 92a of the first alternative embodiment are piezoelectric chips embedded within the foam block 88. Each transducer 92a includes a pair of electrodes on its opposite faces and is encapsulated in an insulating cocoon 108 of epoxy, acrylic, or silicone rubber which prevents the fluid in the foam from creating a short circuit between the electrodes.

A second alternative embodiment of a linear lesion catheter according to the present invention is shown in FIGS. 25 and 26. The second alternative embodiment also differs from the preferred embodiment only in the form and placement of the transducers. Each transducer 92b and its leads 102b is inside an epoxy capsule 109 embedded in the foam block 88. It should be noted, then, that only the RF electrode leads 100 extend through the lumen 98. The leads 102b of the second alternative embodiment extend through fluid lumen 94 as shown.

System Components

Referring to FIG. 1, the system 100 generally includes amplification and localization hardware 110, catheters 10, 12, 14 and 16, and a microprocessor workstation 112.

Hardware 110 includes conventional signal amplifiers 114 of the type used for electrophysiology procedures (for example, the Model 8100/8300 Arrhythmia Mapping System available from Cardiac Pathways Corporation, Sunnyvale, Calif.). It also includes ultrasound ranging hardware 116 and an ultrasound hardware control and timing component 118 which together initiate, detect, and measure the time of flight of ultrasound pulses emitted and received from the ultrasound transducers on the reference and EP catheters 10–16.

Signal amplifiers 114 and the ranging hardware 116 and controller 118 are electronically coupled to a microprocessor workstation 112. The microprocessor work station 112 is designed to control the system hardware and the data processing for both the EP and ultrasound functions of the system, and to generate a visual display of EP and catheter position data for use by the clinician.

For EP functions, the microprocessor 112 includes an amplifier controller 120 that delivers mapping, and/or pacing commands to the EP signal amplifiers 114. Signal processors 122 receive data corresponding to electrical activity measured by the mapping catheters 14, 16 and generate graphical representations of the measured data for display on graphical interface display 124. The mapping signals shown on the graphical display can represent any number of parameters or characteristics, such as measured signal values or impedance values, indicators of electrode contact, or indicators of the probability that there is an arrhythmogenic site in the area, etc.

Ultrasound hardware controller 118 and a triangulation processor 126 control the catheter localization functions and data processing. During use, controller 118 directs the ultrasound ranging hardware 116 to initiate an ultrasound pulse from a selected transmitting transducer. It further directs the hardware 116 to (1) detect, in parallel, voltages corresponding to reception of the ultrasound pulse by the receiving transducers, and (2) measure the elapsed time (time of flight) between transmission of the ultrasound pulse and its detection by the selected receiving transducers. Triangulation processor 126 receives data corresponding to these time of flight measurements from the ranging hardware 116 and uses it to calculate the locations of the EP catheter transducers relative to the reference transducers (see Localization System Overview). Data corresponding to catheter position, as calculated from transducer locations, and measured EP signals is shown in graphical form on graphical user interface display 124.

The ultrasound ranging hardware 116 may be configured to detect an acoustic pulse received by a receiving transducer in a number of ways. For example, if the transmitting transducer is made to generate a short burst of high frequency ultrasound energy, the hardware 116 may be configured to detect the first signal excursion above or below a predetermined maximum and minimum voltage threshold, or the peak of a received signal. Alternatively, the transducer may be made to generate a continuous wave of low frequency ultrasound, in which case the hardware 116 would be configured to measure the difference in phase between the standing wave as generated by the transmitting transducer and as detected by the receiving transducer.

Figure 27A:
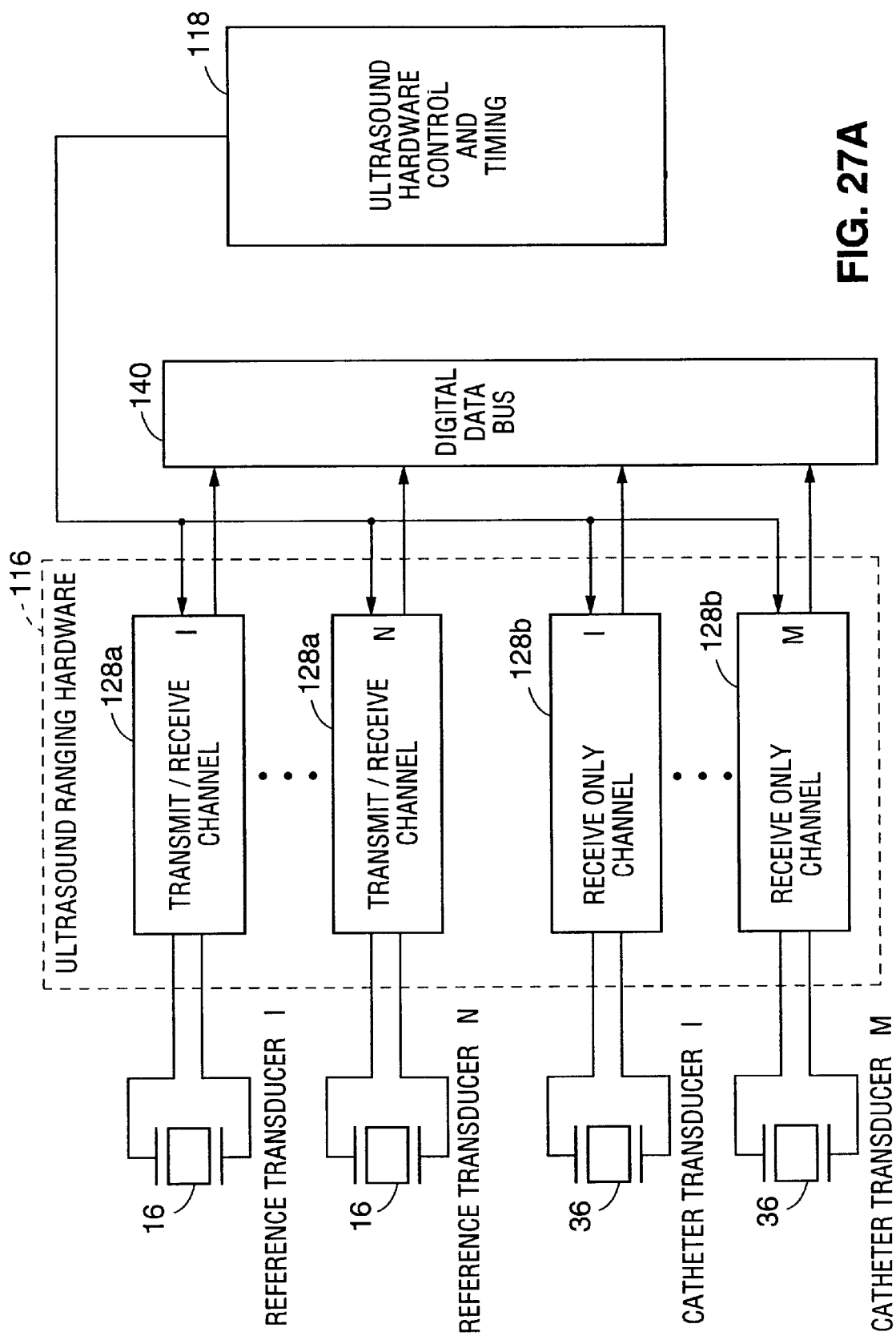
FIG. 27A is a schematic drawing showing ultrasound ranging hardware and its interaction with the ultrasound hardware control and timing systems.

Referring to FIG. 27A, the ultrasound ranging hardware 116 includes a plurality of channels 128a, 128b, each of which is electronically coupled to one of the ultrasound transducers in the system. Depending on whether a transducer is intended to transmit and receive ultrasound signals (as in the case of a reference catheter transducer 18) or to receive ultrasound signals only (as in the case of an additional catheter transducer 34, 58 or 92), a transducer's corresponding channel circuitry may be configured to permit transmission and receipt of ultrasound signals by the transducer, or it may be configured only to allow receipt of signals by the transducer. Accordingly, transmit/receive channels 128a are each connected to a corresponding one of the reference catheter transducers 18 (FIG. 3), and receive channels 128b are each connected to a catheter transducer 34, 58, 92 (e.g., FIGS. 9, 13 and 19).

Figure 27B:
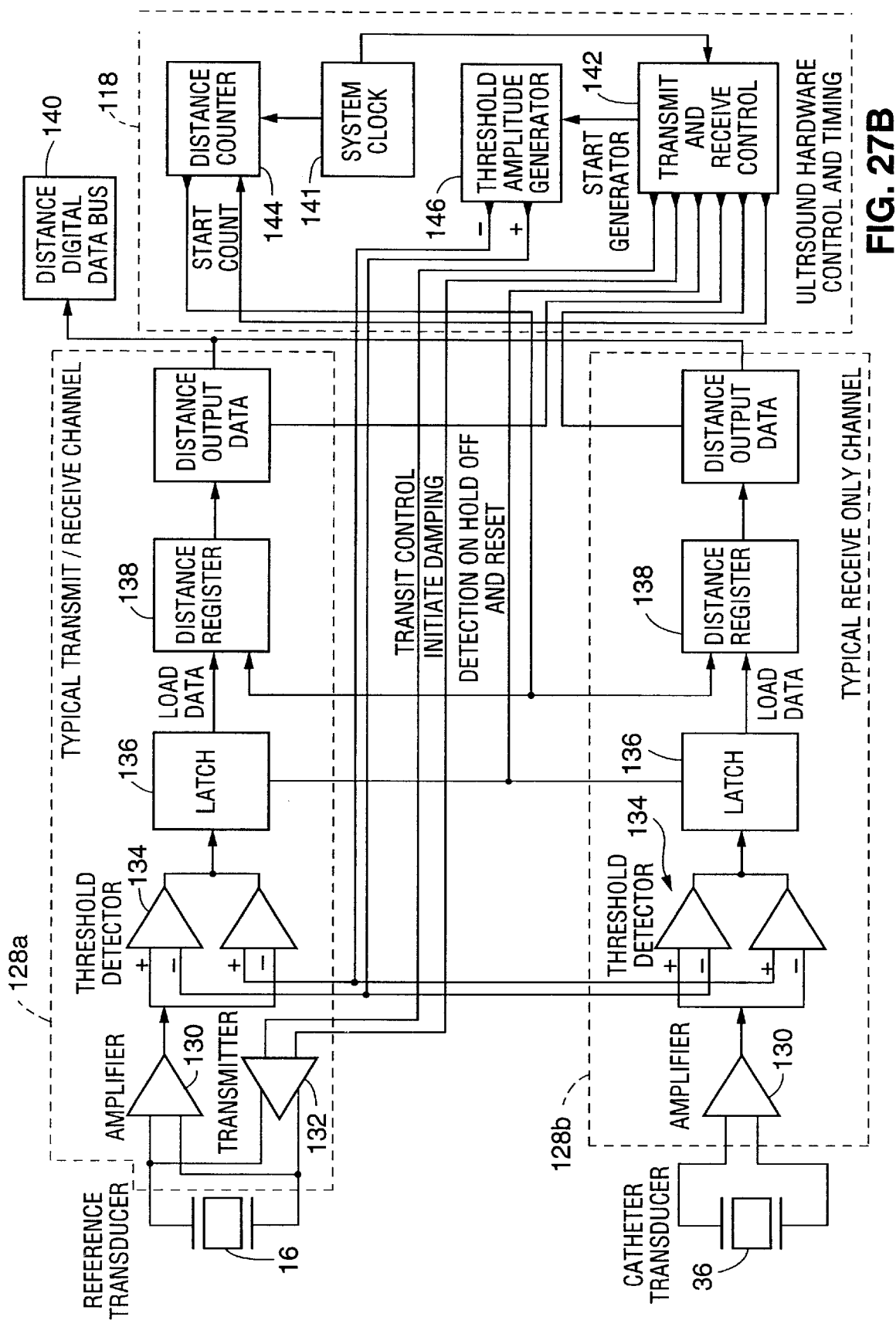
FIG. 27B is a schematic diagram illustrating in greater detail ultrasound ranging hardware and ultrasound hardware control and timing systems of the type shown in FIG. 27A.

Referring to FIG. 27B, the circuitry of each of the channels 128a, 128b generates digital data corresponding to the time of flight of an ultrasound transmit pulse from a transmitting transducer to the transducers corresponding to each of the channels 128a, 128b. Each channel 128a, 128b includes an amplifier 130 which amplifies voltage signals generated by the ultrasound transducers in response to receive pulses. The transmit/receive channels 128a additionally include transmitters 132 which, in response to signals from transmit and receive controller 142 (discussed below), apply voltages across the reference transducers 18 to trigger ultrasound pulses.

Each channel 128a, 128b further includes a threshold detector 134 which triggers a latch 136 once a received signal exceeds a threshold level. Latch 136 is coupled to distance register 138 which is in turn coupled to place distance output data onto data bus 140 upon activation of the latch 136.

Ultrasound hardware control and timing component 118 includes transmit and receive controller 142. Controller 142 is electronically coupled to a system clock 141 that drives a distance counter 144, and to a threshold amplitude generator 146 which provides the threshold reference input for threshold detectors 134.

As will be discussed in greater detail, count values from the distance counter 144 are used by the system of the invention to calculate the distances between transmitting transducers and receiving transducers. Because system clock 141 drives the distance counter 144, it is the frequency of the system clock that determines the resolution of measured distances between transducers. The higher the frequency of the clock, the greater the resolution of the distance measured. Clock 141 is therefore a high frequency counter which preferably operates at least approximately 5–50 MHz, which is equivalent to a resolution of approximately 0.3–0.03 mm.

The threshold amplitude generator 146 produces time varying positive and negative thresholds that are used as inputs to the threshold detectors 134 of each channel 128a, 128b. Preferably, one threshold amplitude generator 146 is used for the entire system in order to minimize the amount of hardware in the system. However, the system may alternatively use a separate threshold amplitude generator for each channel, or separate threshold amplitude generators for different groups of channels. For example, different threshold amplitude generators may be used for different types of receiving transducers, since some produce weaker signals and therefore require lower thresholds. As another alternative, a fixed threshold may be used together with a variable gain amplifier in place of amplifier 130.

The threshold amplitudes are preferably varied by the threshold amplitude generator 146 so that they are large at the time a transmit pulse is initiated and so that they decrease as time passes following transmission of a pulse. Using a variable threshold rather than a fixed one is beneficial because the dynamic range (i.e., the ratio of the largest signal to be detected to the smallest signal to be detected) is quite large, and may even be as high as 70 dB due to factors such as anisotropy of the transit and receive beam profiles, signal decay due to ultrasound wave propagation, and attenuation of the signal caused by blood and tissue. Because transducer receiving wires for a catheter based system must be closely spaced, a fixed dynamic range of this magnitude could lead to erroneous data, because cross-talk between the closely spaced receiving wires could be interpreted by the system to be actual receive signals.

It should be noted that both positive and negative thresholds are used so as to increase the accuracy of the detection time, since a negative oscillation of a transmit pulse may reach the detection threshold before a positive oscillation. Latch 136 will therefore be triggered by whichever of the positive or negative thresholds is achieved first.

Figure 28A:
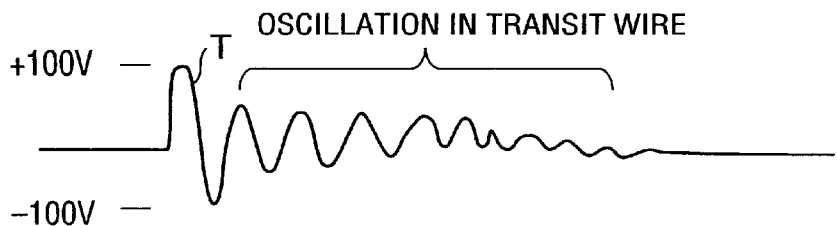
FIG. 28A is a plot of the voltage over time on an ultrasound transmit line following initiation of a transmit pulse, and illustrates the ringing which occurs on the transmit line following the transmit pulse.
Figure 28B:
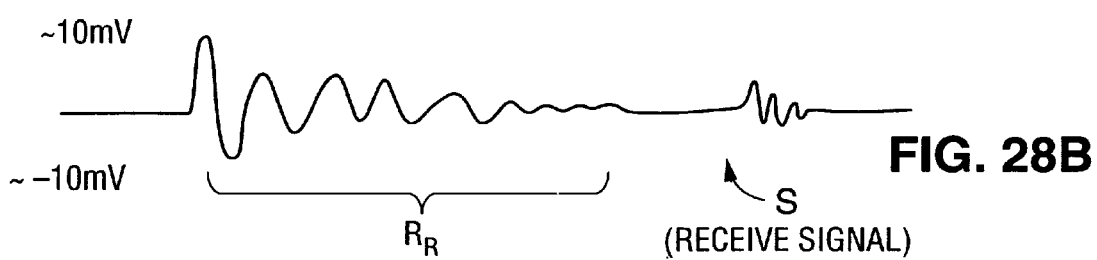
FIG. 28B is a plot of the voltage over time on an ultrasound receive line which is located near the transmit line at the time the transmit pulse of FIG. 28A is initiated. The figure shows the ringing which results from the ringing on the transmit line, and also shows a receive pulse following the ringing.
Figure 28C:
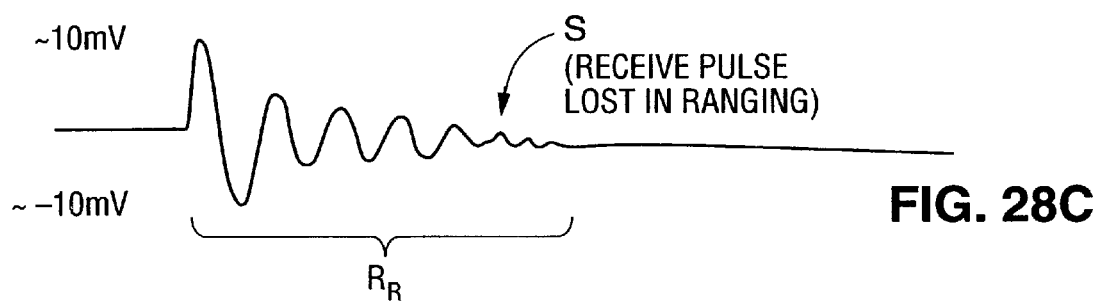
FIG. 28C is a plot of the voltage over time on an ultrasound receive line which is located very close to a transmit wire at the time the transmit pulse of FIG. 28A is instituted, and it illustrates that the receive pulse may be lost in the ringing.

When a transmit pulse T (FIG. 28A) is being sent to a transducer, oscillation, or "ringing", designated "$R_T$", can occur on the corresponding twisted pair 26 (FIG. 3). The ringing in the transmit line is not problematic in and of itself. However, in catheters such as the reference catheter 10 which includes transducers which can both transmit and receive ultrasound signals, the close proximity of the transmitting and receiving lines can cause the ringing to cross over to the receiving line. This problem arises most frequently when the system is computing the relative orientations of the reference transducers 18 (FIG. 3) in order to establish the three-dimensional coordinate system, since that procedure requires measuring the time it takes for a pulse emitted by one of the reference transducers 18 to be received by the other reference transducers 18 on the same catheter. The ringing (which is designated "$R_R$" in FIGS. 28B and 28C) can be of similar magnitude to a receive signal "S" and can therefore make it difficult to determine whether a receive signal has been detected.

If the transmitting and receiving transducers are far apart, a receive signal on a receiving line (such as twisted pair 26) will be measured by the ultrasound system circuitry despite the ringing, because transmission of the receive signal on the receiving line will happen only after the ringing has diminished. See FIG. 28B. However, if the transmitting and receiving transducers are close together (i.e., separated by less than approximately 2 cm), the receive pulse will be lost in the ringing on the receive line, because the receive pulse will reach the receiving line while the ringing is still occurring. See FIG. 28C.

Figure 28D:
FIG. 28D is a plot of the voltage over time on an ultrasound transmit line which is short circuited immediately following the initiation of a transmit pulse.
Figure 28E:
FIG. 28E is a plot of the voltage over time on an ultrasound receive line which is adjacent to the transmit line represented in FIG. 28D. The figure shows that ringing is eliminated on the receive line when the transmit line is short circuited just after the transmit pulse is sent.
Figure 29:
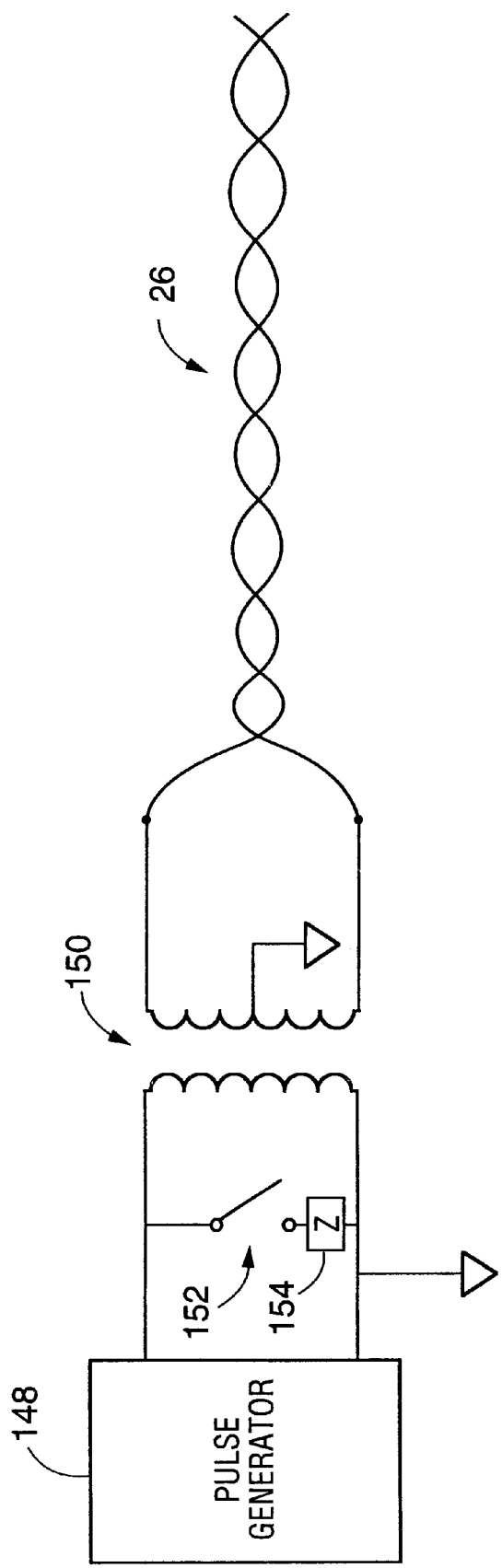
FIG. 29 is a schematic diagram illustrating a pulse generator circuit which includes a switch for short circuiting the transmit line just after the transmit pulse is sent.

It has been found that this problem may be avoided by including circuitry which will short the conductors of the transmit line immediately after the transmit pulse is sent. An example of such circuitry is shown in FIG. 29. The circuit includes the pulse generator 148 and center tapped transformer 150 which comprise basic pulse generating circuitry, plus a switch 152 which is closed immediately after a transmit pulse in order to short the ringing to ground. A small impedance 154 is placed in series with the switch in order to dampen the ringing through the short circuit. As illustrated in FIGS. 28D and 28E, by eliminating the ringing from the transmitting line, the switch eliminates the ringing from the receiving line as well.

Referring again to FIG. 27B, during use of the system, each transmit/receive channel 128a is sequentially selected for transmission of a transmit pulse, and all channels 128a, 128b are simultaneously selected for parallel reception of distance data. Transmit and receive controller 142 selects which of the transmit/receive channel 128a will initiate an ultrasound pulse, and cycles through each transmit/receive channel, causing sequential transmission of pulses by the reference transducers 18 (FIG. 3). It uses the system clock 141 to generate a lower frequency transmit clock, which in turn controls how often ultrasound pulses are transmitted.

Each time a transmit pulse is to be initiated, the transmit and receive controller 142 performs the following sequence of steps. The distance counter 144 is first reset to zero, and the threshold amplitude generator 146 is reset. A detection hold off and reset signal is next sent by controller 142 to all channels 128a, 128b. This resets the latch 136 for each channel and prevents it from latching for a specified time period to prevent detection due to electromagnetic coupling of ringing after transmission of a transmit pulse. This "hold off" period is determined by the smallest distance within the patient that is to be measured, and is calculated according to the following equation:

hold off period=smallest distance*1/(velocity of transmit signal).

Thus, if the smallest distance to be measured is 10 mm, the "hold off period" is:

$$10 \text{ mm} * \frac{1}{1.5 \frac{\text{mm}}{\mu \text{sec}}} = 6.66 \text{ } \mu \text{sec}$$

After the hold off and reset signals, a transmit control signal is sent to a selected one of the transmit/receive channels 128a, causing it to initiate a transmit pulse. Shortly afterwards, a signal is sent to the same transmitter to initiate damping in order to prevent/reduce ringing as described above.

When a transmit pulse is initiated, the distance counter 144 is simultaneously activated. After a transmit pulse is triggered, each channel 128a, 128b "listens for" a receive pulse. When the threshold detector 134 for a particular channel detects a receive pulse that exceeds the threshold set by the threshold amplitude generator 146, the latch 136 for that channel is activated. Once the latch 136 is activated, a load data command is sent to the associated distance register 138 and the current contents of the distance counter 144 are loaded into the distance register 138 for that channel. This data is subsequently placed on the distance data bus 140 along with data indicating which channel transmitted the pulse. Thus, the data bus receives a number of distance values which correspond to the number of transmit/receive and receive only channels. These distance values are then used by the triangulation processor 126 (FIG. 1) to determine the relative positions of the ultrasound transducers, and the microprocessor 112 uses the position data to create a three-dimensional display of the catheters.

Graphical Display Features

As described, the three-dimensional positions of the integrated ultrasound transducers (such as those on catheters 10, 12, 14 and 16) may be continuously displayed in real-time on the graphical user interface display 124 (FIG. 1). The three-dimensional positions of the catheters (10, 12, 14 and 16), or portions thereof, may also or alternatively be continuously displayed based on the position of the transducers by extrapolating the catheter position using a known model of the catheter programmed into the system. The three-dimensional positions of the transducers and/or catheters may also be stored in the system's memory and selectively displayed on the graphical display user interface display 124 as required during a procedure.

For example, data corresponding to electrode locations on a mapping basket 14 may be saved in the system memory, together with data representing EP measurements taken by EP electrodes corresponding to the transducer locations. If, after the mapping basket 14 has been removed from the patient, the user wishes to guide an ablation catheter to a location corresponding to one of the basket electrodes, s/he may elect to display the saved location information for the basket simultaneously with the real time position of the ablation catheter.

The graphical user interface is further provided with several additional functions that improve the accuracy and usefulness of the system.

For example, the microprocessor 112 includes software which enhances the accuracy of the system by "gating out" the effects of cardiac motion on the position data calculated for the transducers and/or catheters. Because a beating heart contracts and expands with each beat, the catheter will move with the heart throughout the cardiac cycle even when a catheter is at a mechanically stable location within the heart. Thus, a real time display of the catheter (or transducer) position would show the catheter or transducer moving on the display because of the cardiac movement.

Such movement of the catheter/transducer on the display does not present problems in and of itself. However, if the user elects to save in the system memory the position of the catheter so that it may be used later during the procedure (such as to indicate anatomical landmarks, ablation locations, mapping locations, etc.), the effects of the movement on the saved locations can lead to inaccuracies if the user attempts to navigate a catheter (shown in real time on the display) with respect to the representation on the graphical display of the previous catheter position data.

To eliminate this problem, the patient's electrocardiogram (EKG) is monitored during use of the system, and the EKG is used to synchronize the acquisition of position data so that all position data is acquired at the same point in the cardiac cycle. Thus, for example, when EP signals are recorded from catheters having integrated localization transducers, the relative position/location information for the EP electrodes is accurate when displayed because all of the location information will have been collected during the same phase of the cardiac cycle. Gating is similarly carried out for the ablation and marking catheters, by collecting the appropriate position/location data for such catheters and the anatomical landmarks during the same phase of the cardiac cycle.

Figure 30A:
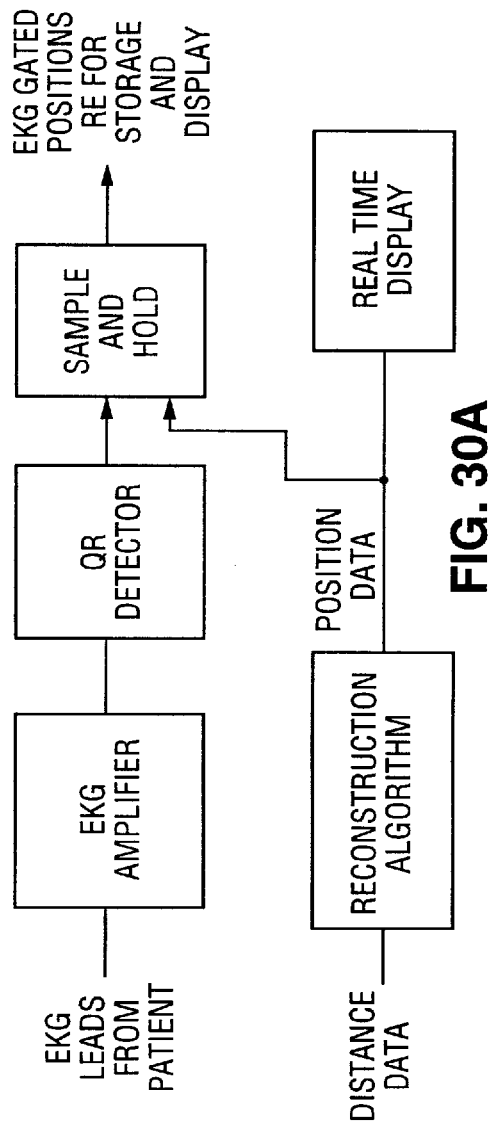
FIG. 30A is a schematic illustration of the sample and hold system used for gating position information to the cardiac cycle.
Figure 30B:
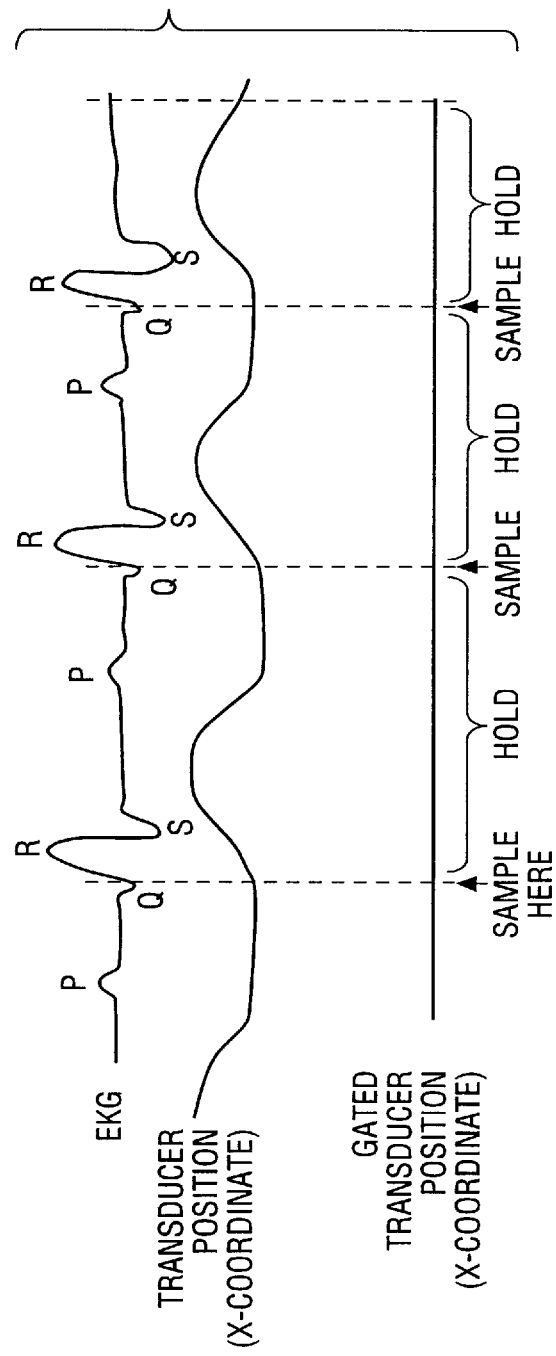
FIG. 30B shows an EKG plot together with a plot of transducer coordinates and illustrates a sample and hold sequence which takes transducer coordinates at the end of diastole.

FIG. 30B shows an EKG signal along with corresponding electrode position data recorded over the cardiac cycle. It has been found that the end of diastole, at the Q-R wave of the EKG signal, is a convenient point for gating the position measurements. FIG. 30A schematically shows a gating system in which a patient's EKG signal is passed through an amplifier 302 and a detector 304 which initiates a sample and hold sequence 306 of position data when the initiation of a Q-R wave is detected.

The user preferably has the option of showing the gated position, or the actual (moving) position, or both on the real time display. The actual position of a catheter may be useful for assessing whether a catheter is in firm contact with the wall of the heart, because if the catheter is spaced away from the wall it will not move with the wall. A display of actual position may also be helpful during steering of a catheter because it provides more rapid feedback of a catheter's position and orientation.

It should be emphasized, however, that gated position information is essential during navigation of a catheter to a location which has been saved in the three-dimensional display, because unless the catheter position and the stored location are gated to the same point in the cardiac cycle, the user cannot be certain that the catheter has been navigated to the proper location.

Similarly, if EP signals are to be displayed in the form of an isochronal map on the three-dimensional display, the position used in the isochronal map to display an activation time for that location should be an EKG gated location.

Similar gating may also be provided to eliminate inaccuracies in location information due to the rising and falling of the chest during respiration. For respiratory gating, chest movement would be monitored using a bellows or other device and the sample and hold sequence would be triggered at a desired portion of the respiratory cycle.

Figure 31:
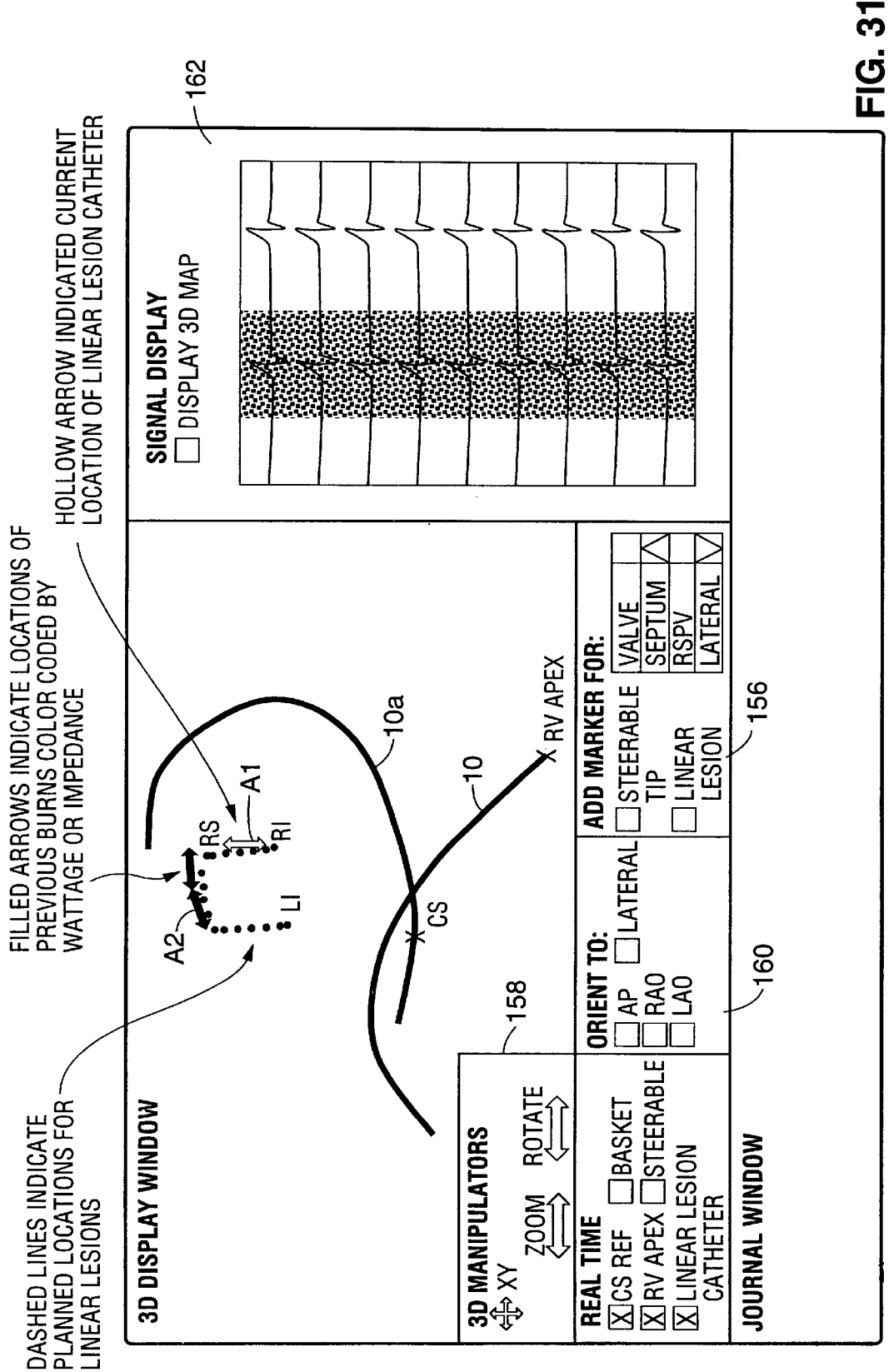
FIGS. 31 and 32 illustrate the graphical user interface of the system according to the present invention.

Referring to FIG. 31, the gated positions of lesions and anatomical landmarks may be stored in the system software and added and deleted from the display as needed by the user by manipulating a cursor using a mouse or other user input device to the appropriate item in marker box 156.

The microprocessor 112 is preferably further provided with software which allows the physician to manipulate the display in many ways so that the maximum benefit may be obtained from the system. For example, referring again to FIG. 31, the user can rotate the display in three-dimensions by guiding the cursor to the appropriate icon in manipulation box 158. The user may likewise "zoom" towards or away from the image in the same manner. S/he may also elect which of the catheters 10, 10a, 12, 16 to display in real time using real time box 156.

The system further allows the user to select one of the standard orientations used in fluoroscopy such as anterior-posterior ("AP"), lateral, right anterior oblique ("RAO") or left anterior oblique ("LAO") by selecting the appropriate icon in orientation box 160. In the RAO view, the plane formed by the aortic-valve ring ("AV ring") is approximately perpendicular to the plane of the display, with the end of the coronary sinus pointing to approximately the 2–3 o'clock position on the AV ring. In the LAO view, the apex of the heart is oriented such that it "points" towards a user viewing the display.

When the system of the invention is used is a preferred mode, the transducers of a reference catheter positioned in the coronary sinus ("CS reference catheter") define the AV ring, and the distal tip of a second reference catheter is positioned in the RV apex ("RV apex catheter"). The system can orient the display to an RAO orientation by deriving the location of the AV ring from the location of the transducers on the CS reference catheter, and re-orienting the display until the AV ring is perpendicular to the display and until the distal tip of the CS reference catheter points towards the 2 o'clock position.

With the AV ring perpendicular to the display, the system may also display straight anterior, posterior, left lateral, and right lateral views by orienting the CS catheter distal tip at the 12 o'clock, 6 o'clock, 3 o'clock, and 9 o'clock positions, respectively.

Similarly, the system can orient the display to an LAO orientation by deriving the location of the RV apex from the locations of the transducers on the RV apex catheter, and by orienting the display so that the RV apex points out of the display.

Operation

Two examples of procedures which may be carried out using the system of the present invention will next be described. It should be appreciated, however, that the system 100 may be utilized in any procedure in which three-dimensional navigation of devices relative to one another is required.

Figure 33:
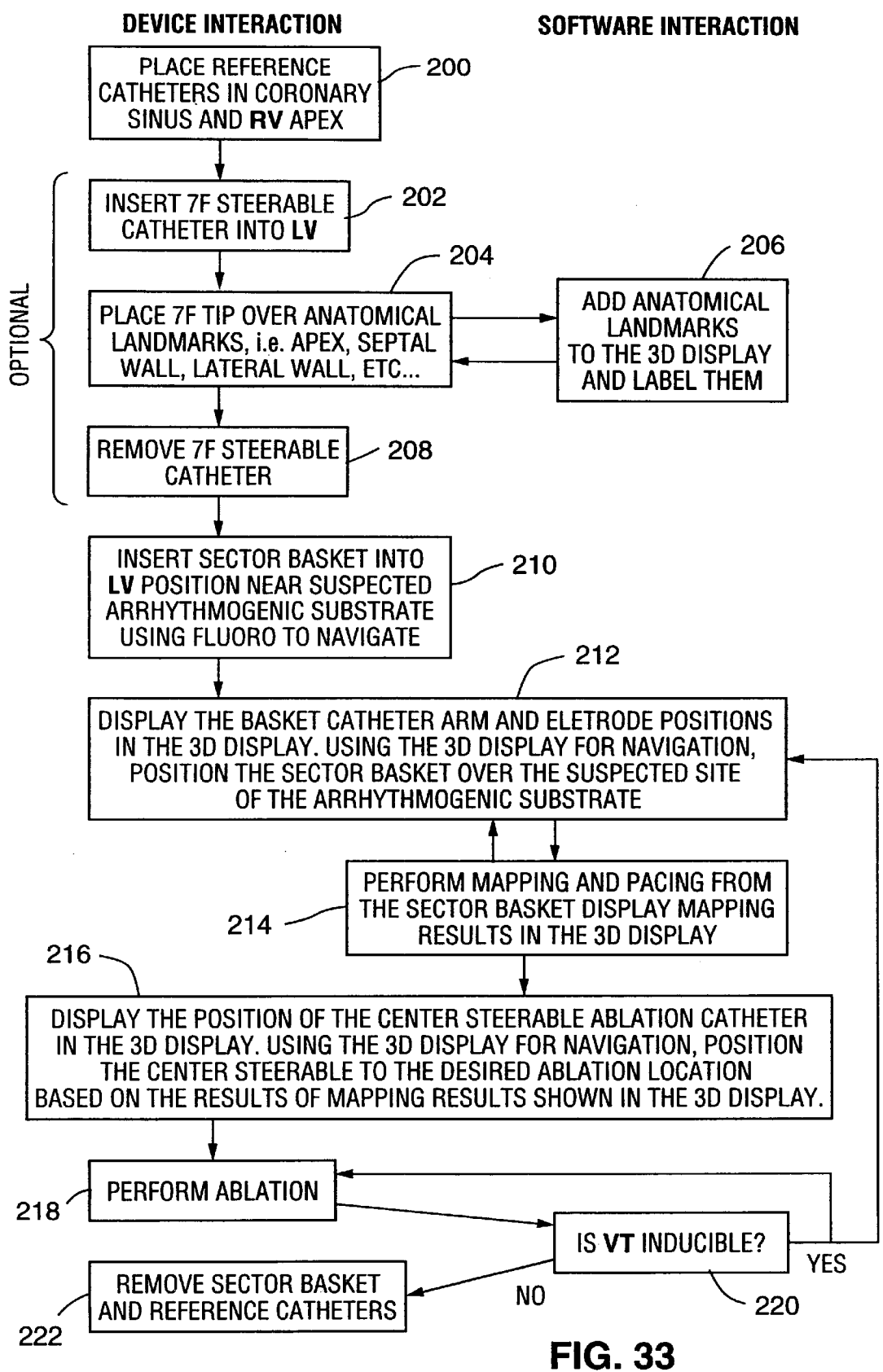
FIG. 33 is a flow diagram illustrating use of the catheters of FIGS. 3, 9 and 13 to treat ventricular tachycardia.

FIG. 33 is a flow diagram giving a sample methodology for using the system according to the present invention for diagnosis and treatment of ventricular tachycardia. The steps shown in the flow diagram will be discussed with reference to the illustrations of the heart shown in FIGS. 34A through 34D.

First, step 200, a reference catheter is introduced into the inferior vena cava and is passed under fluoroscopy into the right ventricle (designated RV). The catheter is positioned with its distal tip at the apex (A). A second reference catheter 10a is introduced via the superior vena cava into the coronary sinus (a vein, shown and designated CS in FIG. 34B, that extends around the edge of the AV ring separating the left atrium and the left ventricle). The reference catheters may be positioned elsewhere without departing from the scope of the present invention. However, the RV and CS are suitable locations because they allow the catheters to remain mechanically stable within the heart. Moreover, these reference catheters will include the EP electrodes equivalent to those already used on CS and RV apex catheters, i.e. they will replace conventional CS and RV apex catheters. Placement of the reference catheters using these approaches therefore does not require introduction of additional introducer sheaths or catheters into the patient.

Throughout the procedure, the system calculates the relative positions of the ultrasound reference transducers 18 (FIG. 3) using time-of-flight measurements and triangulation, establishes the three-dimensional coordinate system, and displays at least a portion of the reference catheter on the graphical interface 124.

Next, referring again to FIG. 34A, marking catheter 12 is preferably (but optionally) introduced into the left ventricle. Catheter 12 is guided under fluoroscopy to sequentially position its distal tip against various anatomical landmarks, such as the apex, septal wall, lateral wall, etc. The location of each transducer 34 (FIG. 9) relative to the reference catheters is calculated again using time-of-flight measurements and triangulation. The location of the catheter distal tip and thus the location of the anatomical site is extrapolated from the transducer location using a model of the catheter 12 pre-programmed into the system, and it may be subsequently displayed on the graphical display. Once the desired landmarks are identified and displayed, the marking catheter 12 is removed from the heart. Steps 202–208.

Figure 34A:
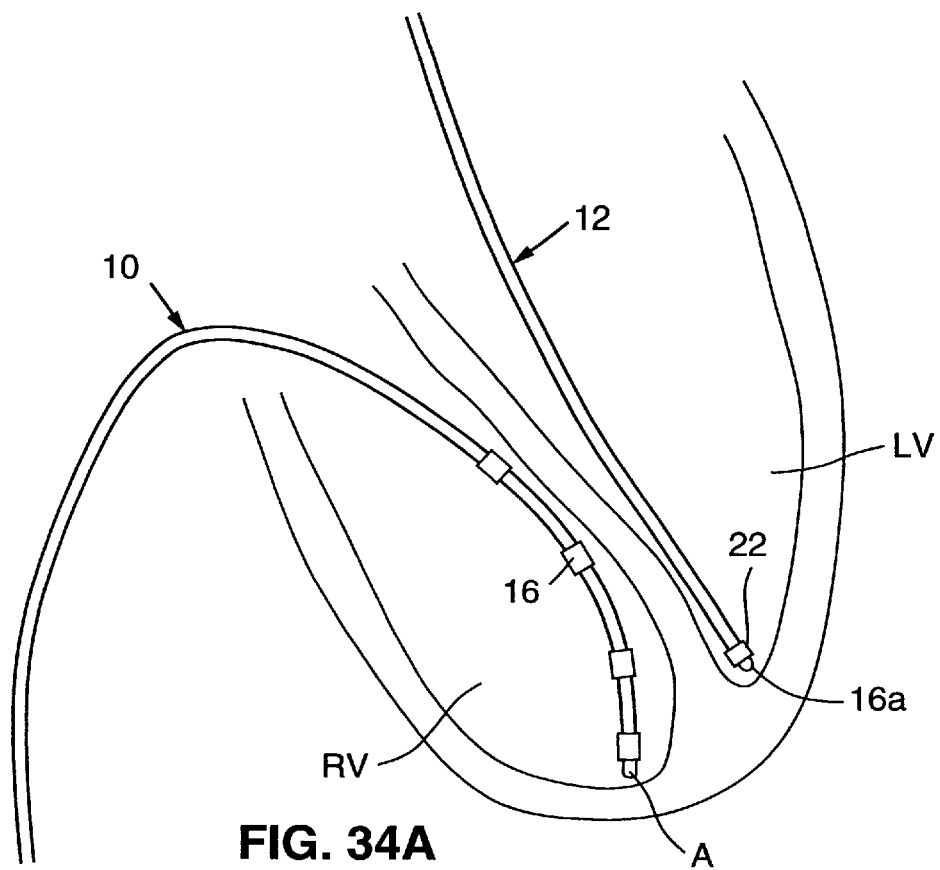
FIGS. 34A–34C are a series of views of a heart illustrating certain of the steps of FIG. 33.
Figure 34B:
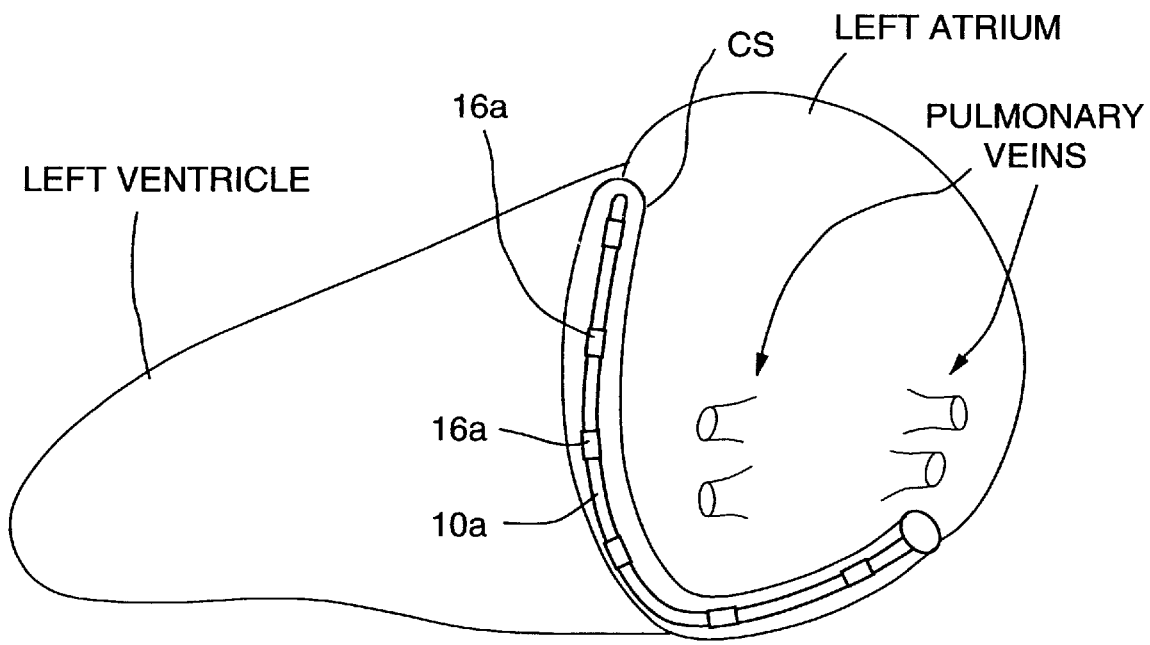
Figure 34C:
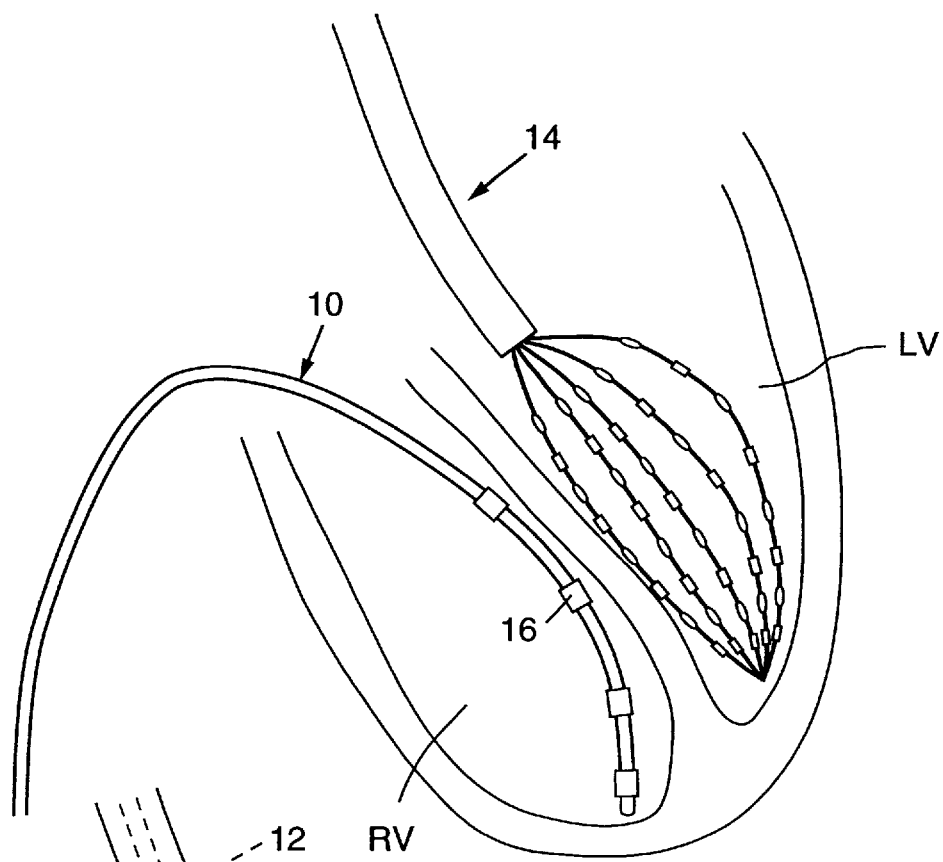

Referring to FIG. 34C, basket catheter 14 (FIG. 13) is next introduced under fluoroscopy into the left ventricle (LV), at a location at which the clinician suspects there may be arrhythmogenic tissue. Step 210. Because the basket arms 52 include ultrasound transducers 58 as well as mapping electrodes 56, the locations of the mapping electrodes can be determined relative to the reference catheters and displayed on the graphical display based on a model of the basket 50 programmed into the system. Step 212.

Electrical activity within the heart is recorded from the mapping electrodes 56 and mapping data derived from the recorded activity is displayed on the graphical display. The EP signal display may be displayed separately from the three-dimensional display, such as in the signal display window 162 shown in FIG. 32. Each graph in the signal display window 162 represents the voltage data over time, as measured by one of the EP electrodes 56 on the basket catheter 14.

The EP signals may alternatively be displayed in the form of an isochronal map on the three-dimensional display. A display of this type would be generated by first placing an activation time on each signal, where an activation time is the time at which the tissue under a mapping electrode 56 activates. The activation times can be either placed automatically using an algorithm or manually by the user. The map is generated by showing a color on the three-dimensional display that represents an activation time at a location corresponding to the location of the electrodes that measured the signal. It may be in the form of discrete color dots or an interpolated color surface or sheet which passes through the locations of the EP electrodes.

The EP display may alternatively take the form of an isopotential display on the three-dimensional display. An isopotential map is similar to an isochronal map except that it is a time varying color display that is proportional to signal amplitude rather than a static display of activation time.

Other mapping data derived from the EP signals may also be shown on the display. For example, data indicating the adequacy of contact between the electrodes and the tissue, or indicating the probability that there is an arrhythmogenic site at the mapped location may be represented on the display. The physician may induce electrical activity for subsequent measurement by pacing the heart from the basket electrodes 56. Step 214.

Figure 34D:
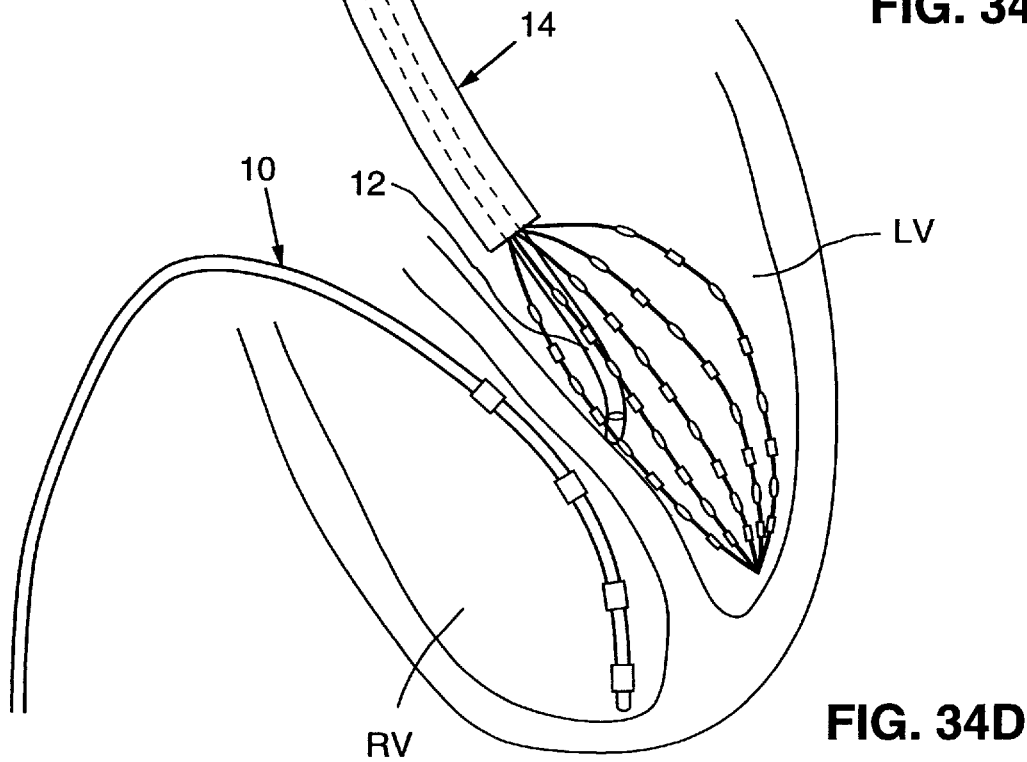
FIG. 34D is a view similar to the view of FIG. 34C showing introduction of an ablation catheter into the mapping catheter.

If an arrhythmogenic region is identified by the clinician on the visual display, a marking and ablation catheter 12 (FIG. 9) is inserted into the center lumen 80 of mapping catheter 14 (FIG. 15) and is guided into the left ventricle. The three-dimensional position of the ablation electrode 36 is displayed (using ultrasound receiving transducer 18 to track its position) in real time to aid the physician in guiding the electrode 36 to the arrhythmogenic region of the endocardium. FIG. 34D and step 216. Once the ablation electrode is positioned at the arrhythmogenic region, ablation is carried out by supplying RF energy to the electrode 36.

The clinician next attempts to induce ventricular tachycardia by pacing the site from the basket catheter electrodes 56 or from electrodes on another catheter. Step 220. If VT cannot be induced, the procedure is considered successful and the catheters 10, 14 are removed. Step 222. If VT is induced, additional mapping and ablation steps are formed until the VT appears to be eradicated.

It should be noted that if mapping is carried out using a basket catheter that is not provided with a center lumen 39, the basket catheter may be removed after its electrode positions and corresponding mapping signals (which may include a visual identification of the arrhythmogenic region) are saved in the system memory, and a separate ablation catheter may be introduced into the heart and guided to the arrhythmogenic region identified on a visual display of the gated positions of the mapping electrodes.

Figure 35:
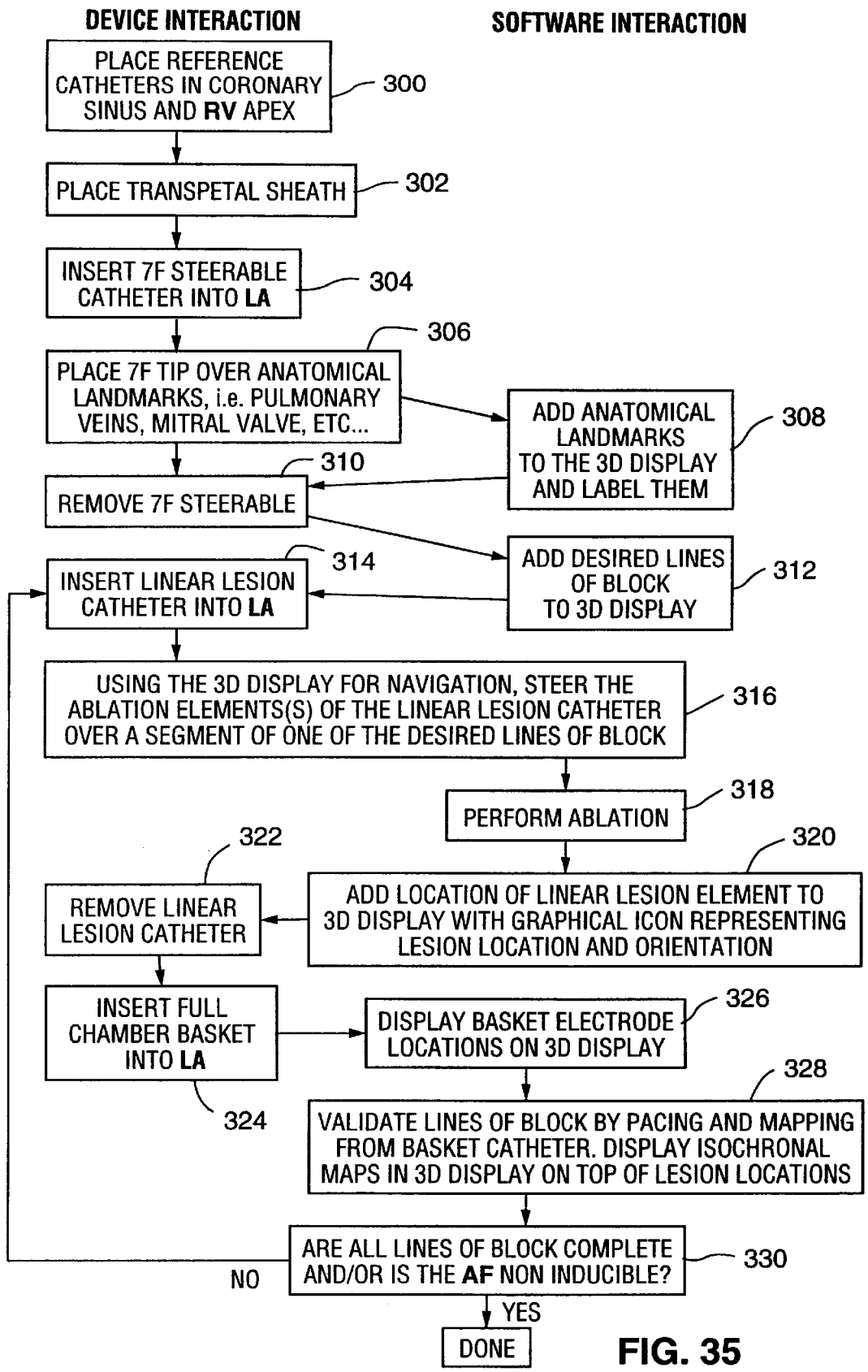
FIG. 35 is a flow diagram illustrating use of the system according to the present invention together with the catheters of FIGS. 3, 9, 13 and 18 to treat atrial fibrillation.

FIG. 35 is a flow diagram illustrating use of the system according to the present invention with a linear lesion catheter of the type shown in FIGS. 18–26 to treat atrial fibrillation. The steps shown in the flow diagram will be discussed with reference to the illustrations of the heart shown in FIGS. 36A–36C and the examples of the graphical user interface shown in FIGS. 31 and 32.

First, reference catheters 10, 10a are placed in the coronary sinus and RV apex as illustrated in FIGS. 34A and 34B. The reference catheters 10, 10a are preferably represented on the graphical display as shown in FIG. 31. Step 300. Although only the reference transducer positions are precisely known, the catheter locations can be estimated using the transducer positions, the known spacing of the transducers along the catheter bodies, and a known model of the catheter.

Figure 36A:
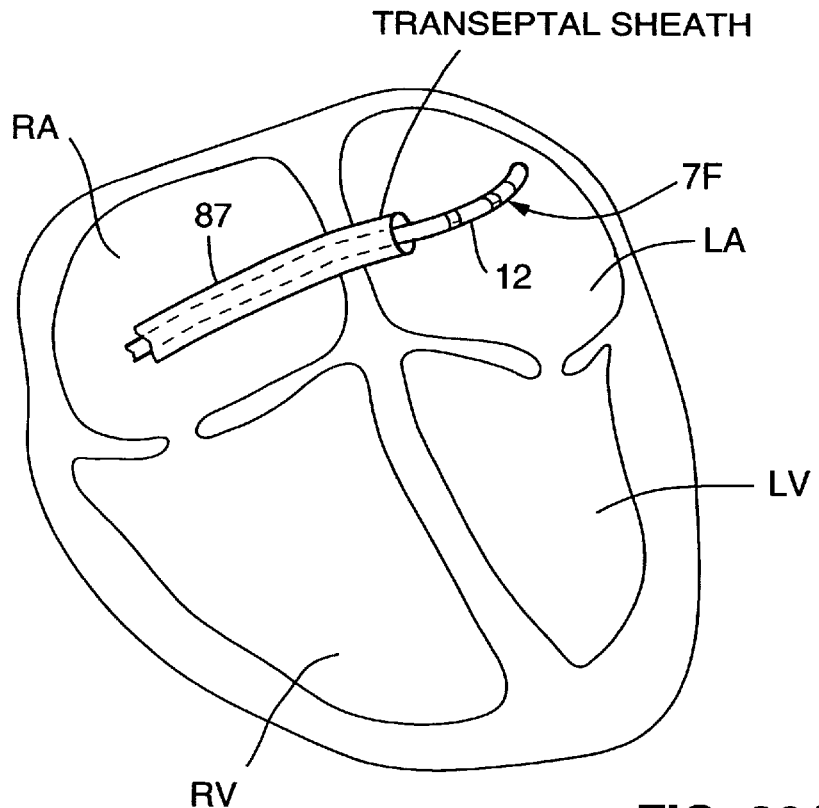
FIGS. 36A–36C are a series of views of a heart illustrating certain of the steps of FIG. 35.

Next, referring to FIG. 36A, marking catheter 12 (FIG. 9) is positioned in the left atrium, preferably by inserting it through a transeptal sheath passed from the right atrium, through the septum and into the left atrium. Steps 302–304. Marking catheter 12 is sequentially positioned with its distal tip at anatomical landmarks, such as the pulmonary veins, septal wall, mitral valve, etc.

The location of each ultrasound transducer 34 on the marking catheter 12 relative to the 3-D coordinate system is calculated using time-of-flight measurements and triangulation. The position of the distal tip is extrapolated from the transducer using a model of the catheter pre-programmed into the system, and is subsequently displayed on the graphical display when the distal tip is positioned at a desired anatomical site (as verified using fluoroscopy), the user adds an appropriate indicator to the display at the distal tip location by entering the necessary input at marker box 156 (FIG. 31). For example, see FIG. 31 in which the left superior pulmonary vein and left inferior pulmonary vein are identified as "LS" and "LI". After the appropriate landmarks are added to the 3-D display, the marking catheter 12 is removed from the heart.

Next, using a mouse or other user input device, lines representing target locations for linear lesions are added to the display. Step 312. These lines are identified by the dashed lines on FIG. 31. The linear lesion catheter 16 (FIG. 8) is next inserted into the left atrium, preferably via the transeptal sheath 87 shown in FIG. 36A. During placement of the linear lesion catheter, the position of ablation window 86 (FIG. 19) is tracked in real time by tracking the positions of the transducers 92 using the localization system 100 and by deriving the window location from the transducer location. An arrow A1 or other icon representing the length of the catheter 16 lying between the transducers 92 is shown on the display as shown in FIG. 31.

Figure 36B:
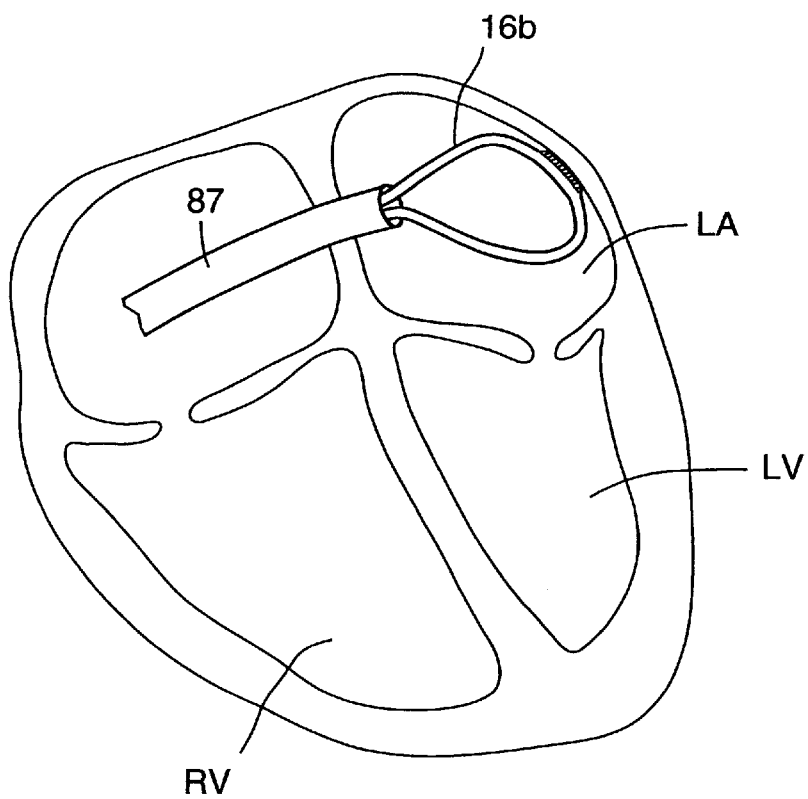

Referring to FIG. 36B, lesion catheter 16b (shown in FIG. 36B to have an ablation section slidable on a looped baffle wire as described in PCT/US96/17536), is guided using the localization system 100 to a first one of the desired ablation locations marked onto the display by the physician. By manipulating the catheter 16 such that the display shows arrow A1 lying over the area marked as a target location, the physician can ensure that the window 86 through which ablation will occur is at the correct location. If a different type of ablation catheter is used, including one which does not involve the use of an electrolytic fluid, the physician may use a similar procedure to align the ablation section (which may be an electrode, an electrode array, or another region of the ablation catheter at which ablation will be carried out) with the target location.

RF energy is supplied to the RF electrodes 90 (FIG. 19) while a conductive fluid is supplied to the fluid port 96 (FIG. 18), to create a linear lesion in the target tissue. Step 318. Arrows A2 or other icons representing the window 86 positions during each ablation are added to the display to indicate the location of a linear lesion. These arrows may be coded by color or other means to indicate characteristics of the lesion, such as the wattage used to create the lesion or the impedance during the ablation. The linear lesion catheter is then repositioned for additional ablation steps until all of the desired ablation locations have been treated.

Figure 32:
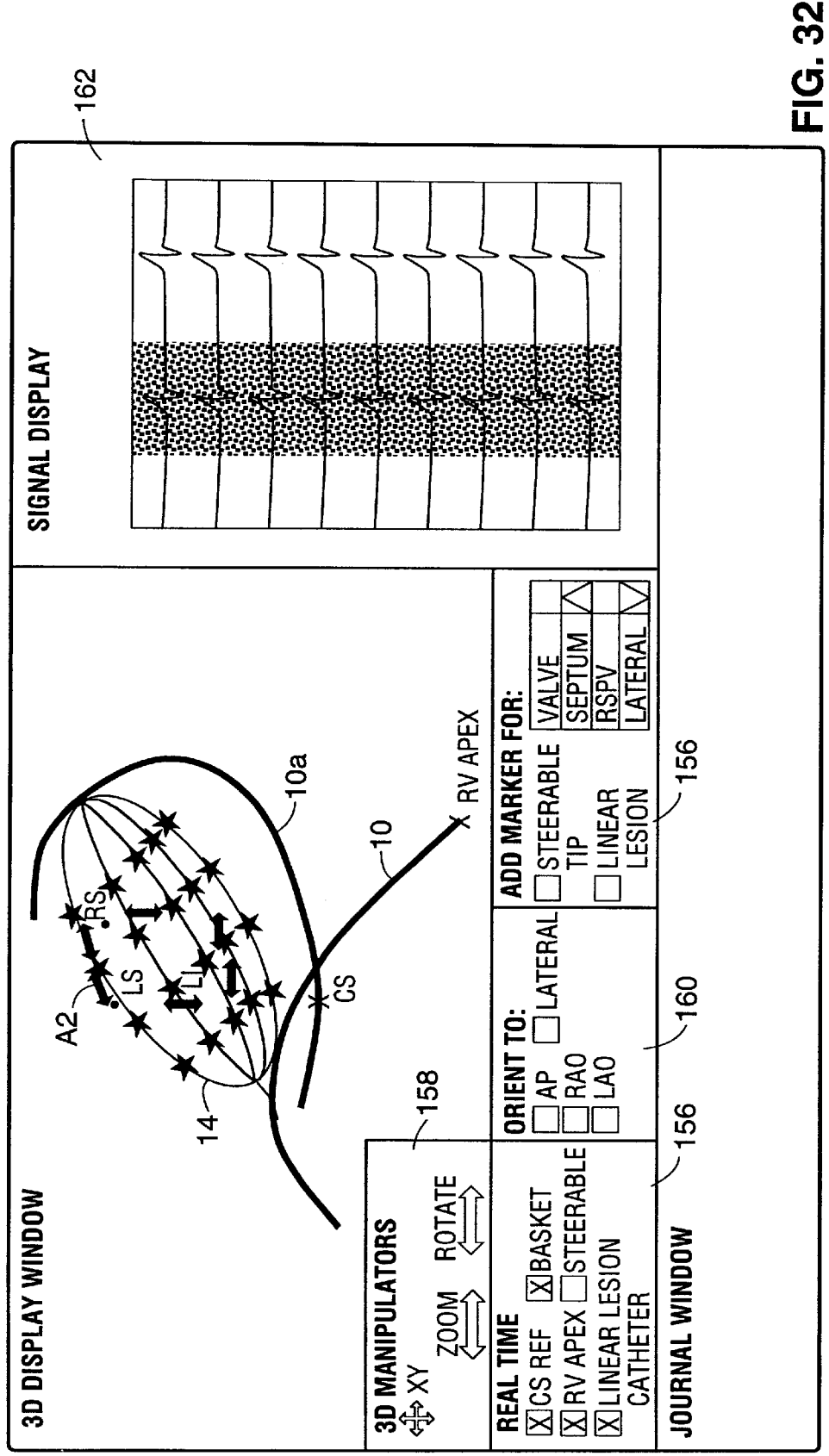
Figure 36C:
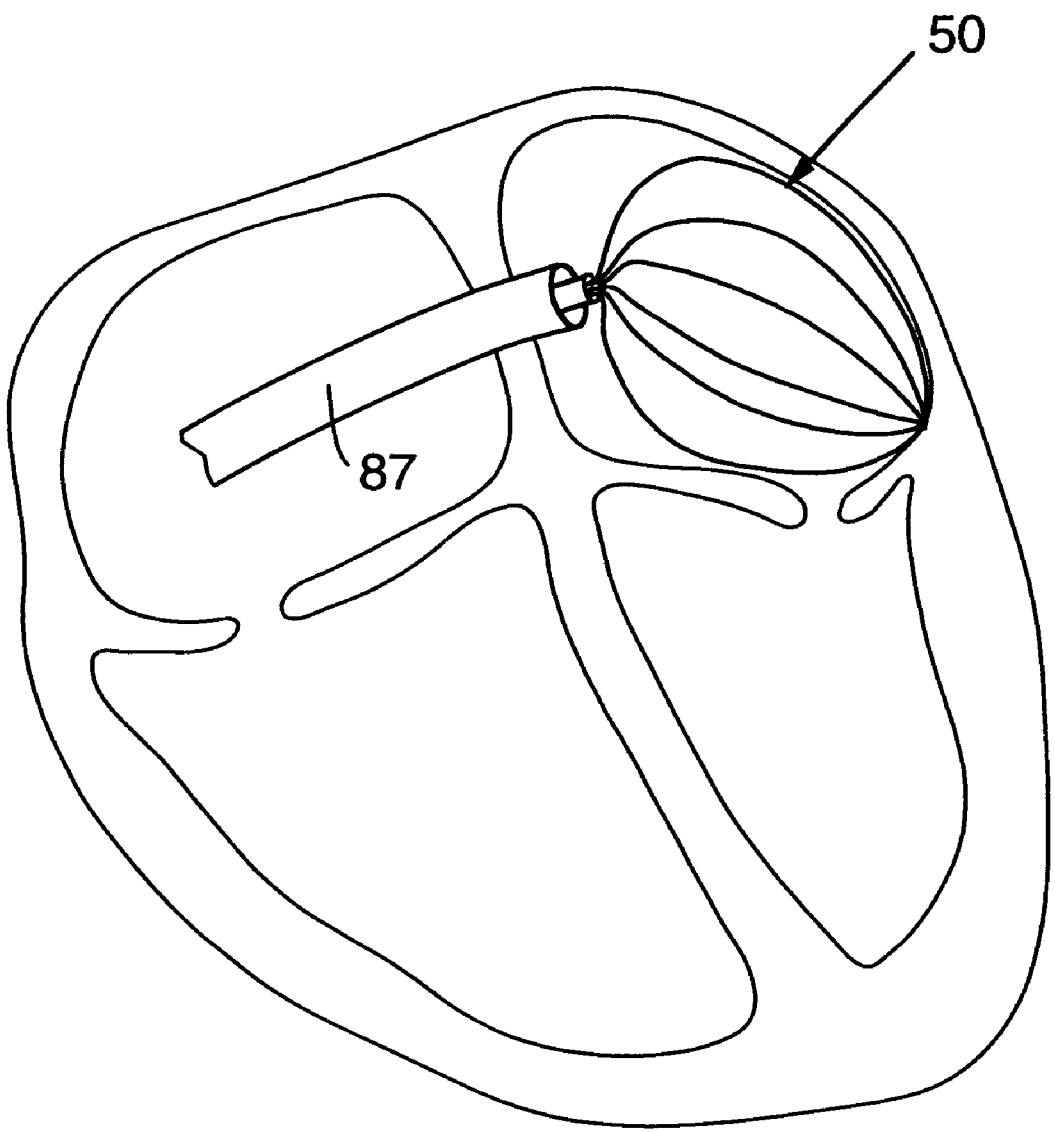

Next, the linear lesion catheter is removed, and mapping basket 50 is inserted into the left atrium as shown in FIG. 36C. Steps 322, 324. The positions of basket electrodes and arms are determined using the ultrasound localization system and are displayed on the 3-D display in the manner described above. FIG. 32 illustrates the positions of the arms 52 with solid lines and the position of the recording electrodes 56 with stars. Pacing and mapping is carried out using the electrodes 56 in a conventional manner to determine whether the linear lesions have blocked transmission of the electrical currents that traverse the left atrium during an atrial fibrillation episode. The electrical activity measured by the mapping electrodes 56 is shown in the form of an isochronal map over the lesion locations A2 on the three-dimensional display. Steps 328–330. If the linear lesions are found to be successful, the basket catheter is removed and the procedure ended. If additional lesions are necessary, the locating, the ablating, pacing and mapping steps are repeated.

One embodiment of the system of the present invention has been described, and it has been described primarily with respect to EP catheters and cardiovascular procedures. It should be appreciated, however, that the system and its components may be used in a variety of medical and non-medical contexts in which three-dimensional representation of structures and surfaces is needed. Thus, the present invention is not to be limited by the specific embodiments and procedures described herein, but should be defined only in terms of the following claims.

We claim:

1. A system for tracking the three-dimensional position of a medical device within a living body, comprising:
 a reference catheter having a plurality of ultrasound reference transducers mounted thereon, the reference catheter positionable within the living body;
 an ultrasound target transducer mounted to a medical device which is to be tracked;
 localization hardware electronically coupled to the ultrasound target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a graphical display; and processor means electronically coupled to the localization hardware for calculating distances between the transducers using the measured elapsed time, for determining a three-dimensional arrangement of the transducers, and for generating an image for display on the graphical display representing a three-dimensional position of at least a portion of the medical device.

2. The system of claim 1 wherein the system is for tracking the three-dimensional position of a medical device having a distal tip and wherein the processor means is for generating an image for display on the graphical display representing the three-dimensional position of the distal tip.

3. The system of claim 1 wherein the processor means is for determining the three-dimensional arrangement of the transducers by determining the three-dimensional arrangement of the reference transducers to establish a coordinate system within the body and by determining the three-dimensional position of the target transducer relative to the coordinate system.

4. The system of claim 1 wherein the processor means is further for generating an image for display on the graphical display representing the three-dimensional position of at least a portion of the reference catheter.

5. The system of claim 1 wherein the medical device is a mapping catheter having a mapping electrode.

6. The system of claim 5 wherein the mapping catheter includes a plurality of ultrasound target transducers.

7. The system of claim 5 wherein the mapping catheter includes an elongate shaft, a plurality of arms extending from the shaft, and a plurality of target transducers and mapping electrodes on the arms of the catheter.

8. The system of claim 7 wherein the processor means is further for deriving the three-dimensional positions of the arms and for generating an image for display on the graphical display representing the three-dimensional position of at least a portion of each arm.

9. The system of claim 7 wherein the mapping catheter comprises both the reference catheter and the medical device.

10. The method of claim 5, wherein the mapping and reference catheters are separate.

11. The system of claim 1 wherein the reference catheter is a mapping catheter having at least one electrode.

12. The system of claim 1 wherein the medical device is a catheter having an electrode and wherein the processor means is further for deriving the three-dimensional position of the electrode and for generating an image for display on the graphical display representing the three-dimensional position of the electrode.

13. The system of claim 1 wherein the reference catheter comprises a single spline on which the ultrasound reference transducers are mounted.

14. A system for tracking the three-dimensional position of a medical device within a living body, comprising:

a reference catheter having a plurality of ultrasound reference transducers mounted thereon, the reference catheter positionable within the living body;

an ultrasound target transducer mounted to a medical device which is to be tracked, the medical device having an electrode;

localization hardware electronically coupled to the ultrasound target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a graphical display; and processor means electronically coupled to the localization hardware for calculating distances between the transducers using the measured elapsed time, for establishing a coordinate system using the calculated distances, for determining a three-dimensional position of the target transducer relative to the coordinate system, for using the three-dimensional position of the target transducer to derive a three-dimensional position of the electrode relative to the coordinate system, and for generating an image for display on the graphical display representing a three-dimensional position of the electrode.

15. The system of claim 14 wherein the processor means is further for using the three-dimensional position of the target transducer to derive the three-dimensional position and orientation of the catheter relative to the coordinate system, and for generating an image for display on the graphical display representing the three-dimensional position and orientation of at least a portion of the catheter.

16. The system of claim 14 wherein the reference catheter has an electrode.

17. The system of claim 14 wherein the reference catheter comprises a single spline on which the ultrasound reference transducers are mounted.

18. A system for diagnosing and/or treating cardiac arrhythmias, the system comprising:

a plurality of ultrasound reference transducers, the reference transducers mounted on at least one reference catheter positionable within a patient's chest;

a mapping catheter having a mapping portion including at least one mapping electrode and at least one ultrasound target transducer adjacent to the mapping catheter;

localization hardware electronically coupled to the target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

electrophysiology hardware electronically coupled to the mapping electrode for receiving mapping signals corresponding to electrical activity measured by the mapping electrodes;

a graphical display; and processor means electronically coupled to the localization hardware for calculating distances between the transducers using the measured elapsed time; for determining a three-dimensional arrangement of the transducers, for receiving mapping signals from the electrophysiology hardware, and for generating an image for display on the graphical display representing a three-dimensional position of at least a portion of the mapping catheter.

19. The system of claim 18 wherein the reference catheter has a mapping electrode.

20. The system of claim 18 wherein the processor means is for determining the three-dimensional arrangement of the transducers by determining the three-dimensional arrangement of the reference transducers to establish a coordinate system within the body and by determining the three-dimensional position of the target transducer relative to the coordinate system.

21. The system of claim 18 wherein the processor means further generates data representing the received mapping signals for display on the graphical display.

22. The system of claim 18 wherein the processor means is for displaying the data representing the received mapping signals on the graphical display at a location corresponding to the three-dimensional positions of the mapping electrodes.

23. The system of claim 22 wherein the processor means is for generating an isochronal map displaying the data representing the received mapping signals on the graphical display at a location corresponding to the three-dimensional positions of the mapping electrodes.

24. The system of claim 22 wherein the processor means is for generating an isopotential map displaying the data representing the received mapping signals on the graphical display at a location corresponding to the three-dimensional positions of the mapping electrodes.

25. The system of claim 21 wherein the mapping catheter includes:

an elongate shaft;

a plurality of arms extending from the shaft;

a plurality of the mapping electrodes carried on the arms; and a plurality of ultrasound tracking transducers on the arms.

26. The system of claim 18 wherein:

the system further comprises an ablation catheter having an ablation section, an ablation electrode at the ablation section for forming lesions in the heart, and an ultrasound tracking transducer;

the localization hardware is electronically coupled to the ultrasound tracking transducer on the ablation catheter; and the processor means is further for generating an image which represents the three-dimensional position of at least a portion of the ablation section of the ablation catheter.

27. The system of claim 26 wherein the processor means is further for, with the ablation section at a target location at which a lesion has been formed, using the measured elapsed time for calculating the distances between the ultrasound tracking transducer on the ablation catheter and the other ultrasound transducers, for determining the three-dimensional location of the ablation section using the calculated distances, and for generating an image for selective display on the graphical display which represents the three-dimensional position of at least a portion of the lesion.

28. The system of claim 18 wherein:

the system further comprises a marking catheter having a distal tip and an ultrasound transducer;

the localization hardware is electronically coupled to the ultrasound transducer on the marking catheter;

the processor means is further for deriving the three-dimensional position of the distal tip from the three-dimensional position of the ultrasound transducer on the marking catheter.

29. The system of claim 28 wherein the processor means is further for generating an image which includes the derived three-dimensional position of the distal tip.

30. The system of claim 18 wherein the reference catheter comprises a single spline on which the ultrasound reference transducers are mounted.

31. The method of claim 18, wherein the mapping and reference catheters are separate.

32. An electrode localization and ablation system, comprising:

a reference catheter having a plurality of ultrasound reference transducers mounted thereon, the reference catheter positionable within the living body;

an ablation catheter having an ablation section including at least one ablation electrode for forming lesions and at least one ultrasound target transducer;

localization hardware electronically coupled to the target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a source of ablation energy electrically coupled to the ablation electrode to cause the ablation electrode to generate lesions within the living body;

a graphical display; and processor means electronically coupled to the localization hardware for calculating distances between the transducers using the measured elapsed time, for determining a three-dimensional arrangement of the transducers, and for generating an image for display on the graphical display representing a three-dimensional position of at least a portion of the ablation section.

33. The system of claim 32 wherein the processor means is further for, with the ablation section at a target location at which a lesion has been formed, using the measured elapsed time for calculating the distances between the ultrasound tracking transducer on the ablation catheter and the other ultrasound transducers, for determining the three-dimensional location of the ablation section using the calculated distances, and for generating an image for selective display on the graphical display which represents the three-dimensional position of at least a portion of the lesion.

34. The system of claim 32 wherein the processor means is for determining the three-dimensional arrangement of the transducers by determining the three-dimensional arrangement of the referenc e transducers to establish a coordinate system within the body and by determining the three-dimensional position of the target transducer relative to the coordinate system.

35. The system of claim 32 wherein the reference catheter comprises a single spline on which the ultrasound reference transducers are mounted.

36. A method of tracking the position of a target catheter within a chamber of a living heart, comprising the steps of:

positioning a reference catheter inside the body, near the heart, with the reference catheter having a plurality of ultrasound transducers mounted thereon;

positioning a target catheter within a chamber of the heart, the target catheter having at least one ultrasound transducer mounted thereon;

causing a plurality of the transducers to generate ultrasound signals, causing a plurality of the transducers to receive ultrasound signals, including causing ultrasound reference transducers to receive ultrasound signals emitted by other ultrasound reference transducers, and recording elapsed time between the generation of signals from each transmitting one of the transducers and the receipt of signals by receiving ones of the transducers;

determining a location of the target catheter with respect to the reference catheter based on the recorded times; and displaying a location of at least a portion of the target catheter on a graphical display.

37. The method of claim 36, further comprising the step of using one of the catheters to measure the electrical activity of the heart.

38. The method of claim 36, further comprising the step of using one of the catheters to ablate cardiac tissue.

39. The method of claim 36 wherein the reference catheter is positioned in the heart and/or coronary vasculature.

40. The method of claim 36 wherein the location of the target catheter is determined using a triangulation algorithm.

41. The method of claim 36 wherein the reference catheter comprises a single spline on which the ultrasound reference transducers are mounted.

42. The method of claim 36 wherein the reference catheter is positioned within the coronary sinus of the heart.

43. A method of tracking the position of a medical device within a living body, comprising the steps of:

(a) providing a reference catheter having a plurality of ultrasound reference transducers, each reference transducer capable of transmitting and receiving ultrasound signals;

(b) providing a medical device, the medical device including an ultrasound target transducer;

(c) positioning the reference catheter and the medical device within the living body;

(d) causing a plurality of the transducers to transmit ultrasound signals for receipt by others of the transducers, including causing ultrasound reference transducers to receive ultrasound signals emitted by other ultrasound reference transducers;

(e) measuring elapsed time between transmission of each ultrasound signal emitted in step (d) and its receipt by each of the other transducers, and using the measured elapsed time to determine relative distances between the transducers;

(f) using distances determined in step (e), establishing a three-dimensional arrangement of the reference transducers to establish a coordinate system within the body, and determining a location of the medical device relative to the coordinate system; and (g) displaying a three-dimensional position of at least a portion of the target transducer relative to the coordinate system on a graphical display.

44. The method of claim 43 wherein the medical device provided in step (b) is a mapping catheter having a mapping electrode, and wherein the method further comprises the steps of:

(h) positioning the mapping electrode at a location within the living body;

(i) measuring electrical activity from the electrode; and (j) deriving the three-dimensional position of the electrode from the three-dimensional position of the target transducer and graphically representing mapping signals corresponding to electrical activity measured by the electrode on the graphical display at the three dimensional position of the electrode.

45. The method of claim 44 wherein the mapping catheter provided in step (b) includes multiple mapping electrodes and a plurality of target transducers, and wherein:

step (h) includes simultaneously positioning a plurality of the mapping electrodes at a location;

step (i) includes measuring the electrical activity with the plurality of electrodes; and step (j) includes deriving the three-dimensional positions of the electrodes using the three-dimensional positions of the target transducers and simultaneously displaying electrical activity measured by each of a plurality of the mapping electrodes on the graphical display at the three dimensional position of its corresponding electrode.

46. The method of claim 45 wherein the mapping catheter provided in step (b) includes an elongate shaft, a plurality of arms extending from the shaft, a plurality of mapping electrodes on the arms, and a plurality of ultrasound transducers on the arms, and wherein the reference catheter provided in step (a) comprises the mapping catheter.

47. The method of claim 44 wherein the mapping catheter provided in step (b) includes multiple mapping electrodes and a plurality of target transducers, and wherein:

step (h) includes simultaneously positioning a plurality of the mapping electrodes at a location;

step (i) includes measuring the electrical activity with the plurality of electrodes; and step (j) includes deriving the three-dimensional positions of the electrodes using the three-dimensional positions of the target transducers and graphically displaying parameters derived from the measured electrical activity on the graphical display at the three dimensional position of at least a portion of the electrodes.

48. The method of claim 44, wherein the mapping and reference catheters are separate.

49. The method of claim 43 wherein the medical device provided in step (b) is a mapping catheter having a mapping electrode, and wherein the method further comprises the steps of:

(h) positioning the mapping electrode at a location within the living body;

(i) measuring electrical activity from the electrode; and (j) deriving the three-dimensional position of the electrode from the three-dimensional position of the target transducer and graphically representing parameters derived from the measured electrical activity on the graphical display at the three dimensional position of the electrode.

50. The method of claim 49 wherein:

step (b) further provides a second medical device in the form of an ablation catheter having an ablation section including an ablation electrode and a target transducer, and wherein the method further includes:

(k) evaluating the display created at step (j) to identify a target location for ablation;

(l) moving the ablation catheter towards the target location in the body while tracking the location of the ablation catheter relative to the coordinate system;

(m) graphically representing the location of the ablation section on the graphical display;

(o) while observing the graphical display, repeating steps (l) and (m) until the graphical display shows the ablation section at the target location; and (p) supplying ablation energy to the ablation electrode to induce ablation at the target location.

51. The method of claim 49, wherein the mapping and reference catheters are separate.

52. The method of claim 43 wherein the method is for tracking the position of a catheter within a patient's heart, and wherein:

step (a) provides a reference catheter having a distal tip;

step (c) includes positioning the reference catheter in the right ventricle of the patient's heart with the distal tip at the right ventricular apex.

53. The method of claim 52 wherein;

step (a) provides a second reference catheter;

step (c) includes positioning the second reference catheter in the coronary sinus of the patient's heart.

54. The method of claim 43, wherein the method is for tracking the position of a catheter within a patient's heart, wherein the patient's heart has a cardiac cycle, and wherein the method further comprises the step of storing data representing the three-dimensional position of at least a portion of the catheter at a selected portion of the cardiac cycle.

55. The method of claim 43 wherein the method is for tracking the position of a catheter within a patient's heart, and wherein:

step (a) provides a reference catheter;

step (c) includes positioning the reference catheter in the coronary sinus of the patient's heart.

56. The method of claim 43, further including the step of using the relative distances established in step (e), deriving the three-dimensional position and orientation of the reference catheter and displaying an image representing the three-dimensional position and orientation of at least a portion of the reference catheter on the graphical display.

57. The method of claim 43, further including the step of repeating steps (d) through (g) while moving the medical device to a location within the living body.

58. The method of claim 43 wherein step (e) includes using a triangulation algorithm to determine the location of the target transducer.

59. The method of claim 43 wherein the medical device provided in step (b) is an ablation device having an ablation electrode, and wherein the method further comprises the steps of:

(h) positioning the ablation electrode at a target location within the living body;

(i) delivering ablation energy to the electrode to induce ablation at the target location and to thereby form a lesion; and (j) extrapolating the three-dimensional position of at least a portion of the lesion from the three-dimensional location of the target transducer established in step (f); and (k) including the three-dimensional location of the lesion determined in step (j) on the graphical display.

60. The method of claim 43 wherein the medical device is a marking catheter having a distal portion and wherein the ultrasound tracking transducer is located at the distal portion, and wherein:

step (c) includes manipulating the marking catheter under fluoroscopic visualization to position the target transducer adjacent to a predetermined anatomical structure within the body; and the method further includes the step of extrapolating the position of the anatomical structure from the three-dimensional position of the target transducer determined in step (f) and displaying the three-dimensional position of the anatomical structure on the graphical display.

61. The method of claim 43 wherein the reference catheter comprises a single spline on which the ultrasound reference transducers are mounted.

62. The method of claim 43, wherein the reference catheter is positioned within the coronary sinus of the heart.

63. A system for tracking the three-dimensional position of a medical device within a living body, comprising:

a plurality of reference catheters, each reference catheter having at least one ultrasound reference transducer mounted thereon and being positionable within the living body;

an ultrasound target transducer mounted to a medical device which is to be tracked;

localization hardware electronically coupled to the ultrasound target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a graphical display; and processor means electronically coupled to the localization hardware for calculating distances between the transducers using the measured elapsed time, for determining a three-dimensional arrangement of the transducers, and for generating an image for display on the graphical display representing a three-dimensional position of at least a portion of the medical device.

64. The system of claim 63 wherein at least one of the reference catheters has at least two ultrasound reference transducers thereon.

65. A system for tracking the three-dimensional position of a medical device within a living body, comprising:

a plurality of reference catheters, each having at least one ultrasound transducer mounted thereon, the reference catheters positionable within a living body;

an ultrasound target transducer mounted to a medical device which is to be tracked, the medical device having an electrode;

localization hardware electronically coupled to the ultrasound target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a graphical display; and processor means electronically coupled to the localization hardware for calculating distances between the transducers using the measured elapsed time, for establishing a coordinate system using the calculated distances, for determining a three-dimensional position of the target transducer relative to the coordinate system, for using the three-dimensional position of the target transducer to derive a three-dimensional position of the electrode relative to the coordinate system, and for generating an image for display on the graphical display representing a three-dimensional position of the electrode.

66. The system of claim 65 wherein at least one of the reference catheters has at least two ultrasound transducers thereon.

67. The system of claim 65 wherein each of the reference catheters comprises a single spline on which the ultrasound reference transducers are mounted.

68. A system for diagnosing and/or treating cardiac arrhythmias, the system comprising:

a plurality of reference catheters, each having at least one ultrasound reference transducer mounted thereon, the reference catheters positionable within a patient's chest;

a mapping catheter having a mapping portion including at least one mapping electrode and at least one ultrasound target transducer adjacent to the mapping catheter;

localization hardware electronically coupled to the target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

electrophysiology hardware electronically coupled to the mapping electrode for receiving mapping signals corresponding to electrical activity measured by the mapping electrodes;

a graphical display; and processor means electronically coupled to the localization hardware for calculating distances between the transducers using the measured elapsed time, for determining a three-dimensional arrangement of the transducers, for receiving mapping signals from the electrophysiology hardware, and for generating an image for display on the graphical display representing a three-dimensional position of at least a portion of the mapping catheter.

69. The system of claim 68, wherein at least one of the reference transducers has at least two ultrasound reference transducers thereon.

70. The system of claim 68 wherein each of the reference catheters comprises a single spline on which the ultrasound reference transducers are mounted.

71. An electrode localization and ablation system, comprising:

a plurality of reference catheters, each having at least one ultrasound reference transducer mounted thereon, the reference catheters positionable within a living body;

an ablation catheter having an ablation section including at least one ablation electrode for forming lesions and at least one ultrasound target transducer;

localization hardware electronically coupled to the target and reference transducers for causing a plurality of the ultrasound transducers to transmit ultrasound signals, for causing a plurality of the ultrasound transducers to receive ultrasound signals including for causing ultrasound reference transducers to receive ultrasound signals emitted by other ultrasound reference transducers, and for measuring elapsed time between transmission of ultrasound signals by transmitting transducers and receipt of the signals by receiving transducers;

a source of ablation energy electrically coupled to the ablation electrode to cause the ablation electrode to generate lesions within the living body;

a graphical display; and processor means electronically coupled to the localization hardware for calculating distances between the transducers using the measured elapsed time, for determining a three-dimensional arrangement of the transducers, and for generating an image for display on the graphical display representing a three-dimensional position of at least a portion of the ablation section.

72. The system of claim 71 wherein at least one of the reference catheters has at least two ultrasound reference transducers thereon.

73. The system of claim 71 wherein each of the reference catheters comprises a single spline on which the ultrasound reference transducers are mounted.

74. A method of tracking the position of a target catheter within a chamber of a living heart, comprising the steps of:

positioning a plurality of reference catheters inside the body, near the heart, with each reference catheter having at least one ultrasound mounted thereon;

positioning a target catheter within a chamber of the heart, the target catheter having at least one ultrasound transducer mounted thereon;

causing a plurality of the transducers to generate ultrasound signals, causing a plurality of the transducers to receive ultrasound signals, including causing ultrasound reference transducers to receive ultrasound signals emitted by other ultrasound reference transducers, and recording elapsed time between the generation of signals from each transmitting one of the transducers and the receipt of signals by receiving ones of the transducers;

determining a location of the target catheter with respect to the reference catheter based on the recorded times; and displaying a location of at least a portion of the target catheter on a graphical display.

75. The method of claim 74 where at least one of the reference catheters has at least two ultrasound reference transducers thereon.

76. The method of claim 74 wherein each of the reference catheters comprises a single spline on which the ultrasound reference transducers are mounted.

77. The method of claim 74, wherein one of the reference catheters is positioned within the coronary sinus of the heart.

78. The method of claim 74, wherein one of the reference catheters is positioned within the coronary sinus of the heart, and another of the reference catheters is positioned in the right ventricle of the heart.

79. A method of tracking the position of a medical device within a living body, comprising the steps of:

(a) providing a plurality of reference catheters, each reference catheter including at least one reference transducer capable of transmitting and receiving ultrasound signals;

(b) providing a medical device, the medical device including an ultrasound target transducer;

(c) positioning the reference catheter and the medical device within the living body;

(d) causing a plurality of the transducers to transmit ultrasound signals for receipt by others of the transducers, including causing ultrasound reference transducers to receive ultrasound signals emitted by other ultrasound reference transducers;

(e) measuring elapsed time between transmission of each ultrasound signal emitted in step (d) and its receipt by each of the other transducers, and using the measured elapsed time to determine relative distances between the transducers;

(f) using distances determined in step (e), establishing a three-dimensional arrangement of the reference transducers to establish a coordinate system within the body, and determining a location of the medical device relative to the coordinate system; and (g) displaying a three-dimensional position of at least a portion of the target transducer relative to the coordinate system on a graphical display.

80. The method of claim 79 wherein at least one of the reference catheters has at least two ultrasound reference transducers capable of transmitting and receiving ultrasound signals.

81. The method of claim 79 wherein each of the reference catheters comprises a single spline on which the ultrasound reference transducers are mounted.

82. The method of claim 79, wherein one of the reference catheters is positioned within the coronary sinus of the heart.

83. The method of claim 79, wherein one of the reference catheters is positioned within the coronary sinus of the heart, and another of the reference catheters is positioned in the right ventricle of the heart.

* * * * *